United States Patent
Jewett et al.

(10) Patent No.: US 12,365,930 B2
(45) Date of Patent: *Jul. 22, 2025

(54) METHOD FOR RAPID IN VITRO SYNTHESIS OF GLYCOPROTEINS VIA RECOMBINANT PRODUCTION OF N-GLYCOSYLATED PROTEINS IN PROKARYOTIC CELL LYSATES

(71) Applicants: Northwestern University, Evanston, IL (US); Cornell University, Ithaca, NY (US)

(72) Inventors: Michael Christopher Jewett, Evanston, IL (US); Jessica Carol Stark, Evanston, IL (US); Matthew P. DeLisa, Ithaca, NY (US); Thapakorn Jaroentomeechai, Ithaca, NY (US)

(73) Assignees: Northwestern University, Evanston, IL (US); Cornell University, Ithaca, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/065,689

(22) Filed: Dec. 14, 2022

(65) Prior Publication Data

US 2023/0279460 A1 Sep. 7, 2023

Related U.S. Application Data

(63) Continuation of application No. 17/077,354, filed on Oct. 22, 2020, now Pat. No. 11,542,538, which is a continuation of application No. 15/650,127, filed on Jul. 14, 2017, now Pat. No. 10,829,795.

(60) Provisional application No. 62/362,327, filed on Jul. 14, 2016.

(51) Int. Cl.
| | |
|---|---|
| *C12P 21/00* | (2006.01) |
| *A61K 38/04* | (2006.01) |
| *A61K 38/16* | (2006.01) |
| *A61K 39/02* | (2006.01) |
| *A61K 39/108* | (2006.01) |
| *C07K 7/06* | (2006.01) |
| *C07K 14/47* | (2006.01) |
| *C12N 1/20* | (2006.01) |
| *C12N 9/10* | (2006.01) |
| *C12P 21/02* | (2006.01) |
| *A61K 39/00* | (2006.01) |
| *C07K 9/00* | (2006.01) |
| *C07K 14/00* | (2006.01) |
| *C12N 1/00* | (2006.01) |
| *C12P 19/00* | (2006.01) |
| *C12R 1/00* | (2006.01) |
| *C12R 1/145* | (2006.01) |
| *C12R 1/19* | (2006.01) |

(52) U.S. Cl.
CPC ............ *C12P 21/005* (2013.01); *A61K 38/04* (2013.01); *A61K 38/16* (2013.01); *A61K 39/0208* (2013.01); *A61K 39/0258* (2013.01); *C07K 7/06* (2013.01); *C07K 14/47* (2013.01); *C12N 1/205* (2021.05); *C12N 9/10* (2013.01); *C12N 9/1081* (2013.01); *C12P 21/02* (2013.01); *C12Y 204/99019* (2015.07); *A61K 2039/6037* (2013.01); *A61K 2039/6068* (2013.01); *C07K 9/00* (2013.01); *C07K 14/00* (2013.01); *C07K 2319/91* (2013.01); *C12N 1/00* (2013.01); *C12P 19/00* (2013.01); *C12P 21/00* (2013.01); *C12R 2001/00* (2021.05); *C12R 2001/145* (2021.05); *C12R 2001/19* (2021.05); *Y02A 50/30* (2018.01)

(58) Field of Classification Search
CPC ........... C12P 21/005; C12Y 204/99019; C12N 1/205; A61K 39/0258
See application file for complete search history.

(56) References Cited

U.S. PATENT DOCUMENTS

| | | | |
|---|---|---|---|
| 4,496,538 | A | 1/1985 | Gordon |
| 4,727,136 | A | 2/1988 | Jennings et al. |
| 5,478,730 | A | 12/1995 | Alakhov et al. |

(Continued)

FOREIGN PATENT DOCUMENTS

| | | |
|---|---|---|
| JP | 2002540075 A | 11/2002 |
| WO | 2003/056914 A1 | 7/2003 |

(Continued)

OTHER PUBLICATIONS

Guarino 2013 (Investigating Oligosaccharyltransferases of N-linked Glycosylation using *Escherichia coli*; PhD Dissertation; Cornell University) (Year: 2013).*

(Continued)

*Primary Examiner* — Mary Maille Lyons
(74) *Attorney, Agent, or Firm* — Quarles & Brady LLP

(57) ABSTRACT

Disclosed are methods, systems, components, and compositions for cell-free synthesis of glycosylated proteins. The glycosylated proteins may be utilized in vaccines, including anti-bacterial vaccines. The glycosylated proteins may include a bacterial polysaccharide conjugated to a carrier, which may be utilized to generate an immune response in an immunized host against the polysaccharide conjugated to the carrier. The glycosylated proteins may be synthesized in cell-free glycoprotein synthesis (CFGpS) systems using prokaryote cell lysates that are enriched in components for glycoprotein synthesis such as oligosaccharyltransferases (OSTs) and lipid-linked oligosaccharides (LLOs) including OSTs and LLOs associated with synthesis of bacterial O antigens.

21 Claims, 6 Drawing Sheets

Specification includes a Sequence Listing.

(56) References Cited

U.S. PATENT DOCUMENTS

| | | | |
|---|---|---|---|
| 5,556,769 | A | 9/1996 | Wu et al. |
| 5,623,057 | A | 4/1997 | Marburg et al. |
| 5,665,563 | A | 9/1997 | Beckler |
| 5,679,352 | A | 10/1997 | Chong et al. |
| 6,168,931 | B1 | 1/2001 | Swartz et al. |
| 6,248,334 | B1 | 6/2001 | Lees et al. |
| 6,531,131 | B1 | 3/2003 | Gu et al. |
| 6,869,774 | B2 | 3/2005 | Endo |
| 6,994,986 | B2 | 2/2006 | Swartz et al. |
| 7,118,883 | B2 | 10/2006 | Inoue et al. |
| 7,189,528 | B2 | 3/2007 | Higashide et al. |
| 7,338,789 | B2 | 3/2008 | Swartz et al. |
| 7,387,884 | B2 | 6/2008 | Suzuki et al. |
| 7,399,610 | B2 | 7/2008 | Shikata et al. |
| 8,703,471 | B2 | 4/2014 | Aebi et al. |
| 8,999,668 | B2 | 4/2015 | DeLisa et al. |
| 10,829,795 | B2 * | 11/2020 | Jewett ............... C12P 21/02 |
| 11,453,901 | B2 * | 9/2022 | Jewett ............... C12N 15/62 |
| 11,530,432 | B2 * | 12/2022 | Jewett ............... C12N 9/1081 |
| 11,542,538 | B2 * | 1/2023 | Jewett ............... A61K 38/04 |
| 2004/0209321 | A1 | 10/2004 | Swartz et al. |
| 2005/0054044 | A1 | 3/2005 | Swartz et al. |
| 2005/0170452 | A1 | 8/2005 | Wildt et al. |
| 2006/0211085 | A1 | 9/2006 | Bobrowicz et al. |
| 2006/0234345 | A1 | 10/2006 | Schwartz et al. |
| 2006/0252672 | A1 | 11/2006 | Betenbaugh et al. |
| 2006/0257399 | A1 | 11/2006 | Gerngross et al. |
| 2006/0286637 | A1 | 12/2006 | Hamilton et al. |
| 2007/0026485 | A1 | 2/2007 | DeFrees et al. |
| 2007/0154983 | A1 | 7/2007 | Calhoun et al. |
| 2007/0178551 | A1 | 8/2007 | Gerngross |
| 2008/0138857 | A1 | 6/2008 | Swartz et al. |
| 2012/0171720 | A1 | 7/2012 | Church et al. |
| 2014/0045267 | A1 | 2/2014 | Lajoie et al. |
| 2014/0255987 | A1 | 9/2014 | Delisa |
| 2014/0295492 | A1 | 10/2014 | Jewett |
| 2015/0259757 | A1 | 9/2015 | Jewett et al. |
| 2018/0016612 | A1 | 1/2018 | Jewett |
| 2018/0298416 | A1 | 10/2018 | Jewett et al. |
| 2019/0284600 | A1 | 9/2019 | Jewett et al. |

FOREIGN PATENT DOCUMENTS

| | | | |
|---|---|---|---|
| WO | 2004/013151 A1 | 2/2004 | |
| WO | 2004/035605 A2 | 4/2004 | |
| WO | 2006/102652 A2 | 9/2006 | |
| WO | 2006/119987 A2 | 11/2006 | |
| WO | 2007/120932 A2 | 10/2007 | |
| WO | 2016023018 A2 | 2/2016 | |
| WO | WO-2017117539 A1 * | 7/2017 | ........... C07K 14/473 |

OTHER PUBLICATIONS

Merritt et al. 2013 (Glycans-By-Design: Engineering Bacteria for the Biosynthesis of Complex Glycans and Glycoconjugates; Biotechnology and Bioengineering 110(6): 1550-1564) (Year: 2013).*

Jaroentomeechai et al. 2018 (Single-pot glycoprotein biosynthesis using a cell-free transcription-translation system enriched with glycosylation machinery; Nature Communications 9:2686: 1-11) (Year: 2018).*

Webster et al. 2021 (The intricate relationship between transcription and translation; PNAS 118(21): e2106284118) (Year: 2021).*

Weerapana, E. and B. Imperiali, Asparagine-linked protein glycosylation: from eukaryotic to prokaryotic systems. Glycobiology, 2006. 16(6): p. 91R-101R.

Weintraub, A. (2003). Immunology of bacterial polysaccharide antigens. Carbohydr Res 338, 2539-2547.

Wetter, M., Kowarik, M., Steffen, M., Carranza, P., Corradin, G., and Wacker, M. (2013). Engineering, conjugation, and immunogenicity assessment of Escherichia coli O121 O antigen for its potential use as a typhoid vaccine component. Glycoconj J 30, 511-522.

WHO (2014). Temperature Sensitivity of Vaccines.

Wilson, I.B., Y. Gavel, and G. von Heijne, Amino acid distributions around O-linked glycosylation sites. Biochem J, 1991. 275 ( Pt 2): p. 529-34.

Xu, Y., et al. Production of bispecific antibodies in "Knobs-into-Holes" using a cell-free expression system. in mAbs. 2014. Taylor & Francis.

Young, N.M., et al., Structure of the N-linked glycan present on multiple glycoproteins in the Gram-negative bacterium, Campylobacter jejuni. Journal of Biological Chemistry, 2002. 277(45): p. 42530-9.

Zalkin, H., C. Yanofsky, and C.L. Squires, Regulated in vitro synthesis of Escherichia coli tryptophan operon messenger ribonucleic acid and enzymes. J Biol Chem, 1974. 249(2): p. 465-75.

Zawada, J.F., et al., Microscale to manufacturing scale-up of cell-free cytokine production—a new approach for shortening protein production development timelines. Biotechnol Bioeng, 2011. 108(7): p. 1570-8.

Zimmerman, E.S., et al., Production of Site-Specific Antibody-Drug Conjugates Using Optimized Non-Natural Amino Acids in a Cell-Free Expression System. Bioconjugate Chemistry, 2014. 25(2): p. 351-361.

Forsgren et al., Protein D of Haemophilus influenzae: A Protective Nontypeable H. influenzae Antigen and a Carrier for Pneumococcal Conjugate Vaccines, Clinical Infectious Diseases, vol. 46, n. 5, Mar. 1, 2008 (Mar. 1, 2008), pp. 726-731.

International Search Report, corresponding to PCT/US2020/013207, Apr. 30, 2020, 2 ppgs.

Office Action, corresponding to JP 2021-540255, dated Dec. 12, 2023.

Novak, R.T., Kambou, J.L., Diomande, F.V., Tarbangdo, T.F., Ouedraogo-Traore, R., Sangare, L., Lingani, C., Martin, S.W., Hatcher, C., Mayer, L.W., et al. (2012). Serogroup A meningococcal conjugate vaccination in Burkina Faso: analysis of national surveillance data. Lancet Infect Dis 12, 757-764.

Ohtsubo, K. and J.D. Marth, Glycosylation in cellular mechanisms of health and disease. Cell, 2006. 126(5): p. 855-67.

Olivier, N.B., et al., In vitro biosynthesis of UDP-N, N'-diacetylbacillosamine by enzymes of the Campylobacter jejuni general protein glycosylation system. Biochemistry, 2006. 45(45): p. 13659-69.

Ollis, A.A., et al., Engineered oligosaccharyltransferases with greatly relaxed acceptor-site specificity. Nat Chem Biol, 2014. 10(10): p. 816-22.

Ollis, A.A., et al., Substitute sweeteners: diverse bacterial oligosaccharyltransferases with unique N-glycosylation site preferences. Sci Rep, 2015. 5: p. 15237.

Oyston, P.C., A. Sjostedt, and R.W. Titball, Tularaemia: bioterrorism defence renews interest in Francisella tularensis. Nat Rev Microbiol, 2004. 2(12): p. 967-78.

Oza, J.P., et al., Robust production of recombinant phosphoproteins using cell-free protein synthesis. Nature Communications, 2015. 6: p. 8168.

Pardee, K., Slomovic, S., Nguyen, Peter Q., Lee, Jeong W., Donghia, N., Burrill, D., Ferrante, T., McSorley, Fern R., Furuta, Y., Vernet, A., et al. (2016). Portable, on-demand biomolecular manufacturing. Cell 167, 248-259.e212.

Perez, C., et al., Structure and mechanism of an active lipid-linked oligosaccharide flippase. Nature, 2015. 524(7566): p. 433-8.

Perez, J.G., J.C. Stark, and M.C. Jewett, Cell-free synthetic biology: Engineering beyond the cell. Cold Spring Harb. Perspect. Biol., 2016.

Perez-Pinera, P., Han, N., Cleto, S., Cao, J., Purcell, O., Shah, K.A., Lee, K., Ram, R., and Lu, T.K. (2016). Synthetic biology and microbioreactor platforms for programmable production of biologics at the point-of-care. Nat Commun 7, 12211.

Petsch, D. and F.B. Anspach, Endotoxin removal from protein solutions. J. Biotechnol., 2000. 76(2-3): p. 97-119.

Pinho, S.S. and C.A. Reis, Glycosylation in cancer: mechanisms and clinical implications. Nat Rev Cancer, 2015. 15(9): p. 540-55.

Poehling, K.A., Talbot, T.R., Griffin, M.R., Craig, A.S., Whitney, C.G., Zell, E., Lexau, C.A., Thomas, A.R., Harrison, L.H., Reingold, A.L., et al. (2006). Invasive pneumococcal disease among infants before and after introduction of pneumococcal conjugate vaccine. JAMA 295, 1668-1674.

(56) References Cited

OTHER PUBLICATIONS

Prior, J.L., et al., Characterization of the O antigen gene cluster and structural analysis of the O antigen of *Francisella tularensis* subsp. *tularensis*. J Med Microbiol, 2003. 52(Pt 10): p. 845-51.
Qadri, F., Svennerholm, A.M., Faruque, A.S., and Sack, R.B. (2005). Enterotoxigenic *Escherichia coli* in developing countries: epidemiology, microbiology, clinical features, treatment, and prevention. Clin Microbiol Rev 18, 465-483.
Raetz, C.R., and Whitfield, C. (2002). Lipopolysaccharide endotoxins. Annu Rev Biochem 71, 635-700.
Raman, R., et al., Glycomics: an integrated systems approach to structure-function relationships of glycans. Nat Methods, 2005. 2(11): p. 817-24.
Ravenscroft, N., et al., Purification and characterization of a Shigella conjugate vaccine, produced by glycoengineering *Escherichia coli*. Glycobiology, 2015.
Riddle, M.S., Kaminski, R.W., Di Paolo, C., Porter, C.K., Gutierrez, R.L., Clarkson, K.A., Weerts, H.E., Duplessis, C., Castellano, A., Alaimo, C., et al. (2016). Safety and immunogenicity of a candidate bioconjugate vaccine against Shigella flexneri 2a administered to healthy adults: a single blind, randomized phase I study. Clin Vaccine Immunol.
Rietschel, E.T., et al., Bacterial endotoxin: molecular relationships of structure to activity and function. FASEB J., 1994. 8(2): p. 217-25.
Roush, S.W., McIntyre, L., and Baldy, L.M. (2008). Manual for the surveillance of vaccine-preventable diseases. Atlanta: Centers for Disease Control and Prevention, 4.
Russell, J.A., Management of sepsis. N. Engl. J. Med., 2006. 355(16): p. 1699-1713.
Saldias, M.S., X. Ortega, and M.A. Valvano, Burkholderia cenocepacia O antigen lipopolysaccharide prevents phagocytosis by macrophages and adhesion to epithelial cells. J Med Microbiol, 2009. 58(Pt 12): p. 1542-8.
Salehi, A.S., et al., *Escherichia coli*-based cell-free extract development for protein-based cancer therapeutic production. Int J Dev Biol, 2016. 60(7-8-9): p. 237-243.
Salehi, A.S., Smith, M.T., Bennett, A.M., Williams, J.B., Pitt, W.G., and Bundy, B.C. (2016). Cell-free protein synthesis of a cytotoxic cancer therapeutic: Onconase production and a just-add-water cell-free system. Biotechnol J 11, 274-281.
Schoborg, J.A., Hershewe, J.M., Stark, J.C., Kightlinger, W., Kath, J.E., Jaroentomeechai, T., Natarajan, A., DeLisa, M.P., and Jewett, M.C. (2017). A cell-free platform for rapid synthesis and testing of active oligosaccharyltransferases. Biotechnol Bioeng.
Schwarz, F., et al., A combined method for producing homogeneous glycoproteins with eukaryotic N-glycosylation. Nat Chem Biol, 2010. 6(4): p. 264-6.
Schwarz, F., et al., Relaxed acceptor site specificity of bacterial oligosaccharyltransferase in vivo. Glycobiology, 2011. 21(1): p. 45-54.
Sleytr, U.B., Heterologous reattachment of regular arrays of glycoproteins on bacterial surfaces. Nature, 1975. 257(5525): p. 400-2.
Spiro, R.G., Protein glycosylation: nature, distribution, enzymatic formation, and disease implications of glycopeptide bonds. Glycobiology, 2002. 12(4): p. 43R-56R.
Stech, M., et al., A continuous-exchange cell-free protein synthesis system based on extracts from cultured insect cells. PLoS One, 2014. 9(5): p. e96635.
Stech, M., et al., Cell-free systems: functional modules for synthetic and chemical biology. Adv Biochem Eng Biotechnol, 2013. 137: p. 67-102.
Stefan, A., Conti, M., Rubboli, D., Ravagli, L., Presta, E., and Hochkoeppler, A. (2011). Overexpression and purification of the recombinant diphtheria toxin variant CRM197 in *Escherichia coli*. J Biotechnol 156, 245-252.

Stefanetti, G., et al., Glycoconjugate vaccine using a genetically modified O antigen induces protective antibodies to Francisella tularensis. Proc. Natl. Acad. Sci. U. S. A., 2019. 116(14): p. 7062-7070.
Szymanski, C.M., et al., Evidence for a system of general protein glycosylation in Campylobacter jejuni. Mol Microbiol, 1999. 32(5): p. 1022-30.
Thanka Christlet, T.H. and K. Veluraja, Database analysis of O-glycosylation sites in proteins. Biophys J, 2001. 80(2): p. 952-60.
The Review on Antimicrobial Resistance, C.b.J.O.N. (2014). Antimicrobial Resistance: Tackling a crisis for the health and wealth of nations.
Theodoratou, E., et al., The role of glycosylation in IBD. Nat Rev Gastroenterol Hepatol, 2014. 11(10): p. 588-600.
Trotter, C.L., McVernon, J., Ramsay, M.E., Whitney, C.G., Mulholland, E.K., Goldblatt, D., Hombach, J., and Kieny, M. P. (2008). Optimising the use of conjugate vaccines to prevent disease caused by Haemophilus influenzae type b, Neisseria meningitidis and *Streptococcus pneumoniae*. Vaccine 26, 4434-4445.
Valderrama-Rincon, J.D., et al., An engineered eukaryotic protein glycosylation pathway in *Escherichia coli*. Nat Chem Biol, 2012. 8(5): p. 434-6.
Valvano, M.A., and Crosa, J.H. (1989). Molecular cloning and expression in *Escherichia coli* K-12 of chromosomal genes determining the O7 lipopolysaccharide antigen of a human invasive strain of *E. coli* O7:K1. Infect Immun 57, 937-943.
Varki, A., Biological roles of oligosaccharides: all of the theories are correct. Glycobiology, 1993. 3(2): p. 97-130.
Wacker, M., et al., N-linked glycosylation in Campylobacter jejuni and its functional transfer into *E. coli*. Science, 2002. 298(5599): p. 1790-3.
Wacker, M., et al., Prevention of *Staphylococcus aureus* infections by glycoprotein vaccines synthesized in *Escherichia coli*. J Infect Dis, 2014. 209(10): p. 1551-61.
Wahl, B., O'Brien, K.L., Greenbaum, A., Majumder, A., Liu, L., Chu, Y., Luksic, I., Nair, H., McAllister, D.A., Campbell, H., et al. (2018). Burden of *Streptococcus pneumoniae* and Haemophilus influenzae type b disease in children in the era of conjugate vaccines: global, regional, and national estimates for 2000-15. Lancet Glob Health 6, e744-e757.
Walt, D., et al., Transforming Glycoscience: A Roadmap for the Future. 2012: The National Academies Press.
Wang, J.Z., I. Grundke-Iqbal, and K. Iqbal, Glycosylation of microtubule-associated protein tau: an abnormal posttranslational modification in Alzheimer's disease. Nat Med, 1996. 2(8): p. 871-5.
Wang, L.X. and B.G. Davis, Realizing the Promise of Chemical Glycobiology. Chem Sci, 2013. 4(9): p. 3381-3394.
Wang, X., et al., Peptide surfactants for cell-free production of functional G protein-coupled receptors. Proc Natl Acad Sci U S A, 2011. 108(22): p. 9049-54.
Hatz, C.F., Bally, B., Rohrer, S., Steffen, R., Kramme, S., Siegrist, C.A., Wacker, M., Alaimo, C., and Fonck, V.G. (2015). Safety and immunogenicity of a candidate bioconjugate vaccine against Shigella dysenteriae type 1 administered to healthy adults: A single blind, partially randomized Phase I study. Vaccine 33, 4594-4601.
Hodgman, C.E. and M.C. Jewett, Cell-free synthetic biology: thinking outside the cell. Metab Eng, 2012. 14(3): p. 261-9.
Hong, S.H., Ntai, I., Haimovich, A.D., Kelleher, N.L., Isaacs, F.J., and Jewett, M.C. (2014). Cell-free protein synthesis from a release factor 1 deficient *Escherichia coli* activates efficient and multiple site-specific nonstandard amino acid incorporation. ACS Synth Biol 3, 398-409.
Humphreys, G. (2011). Vaccination: rattling the supply chain (Bulletin of the World Health Organization: World Health Organization).
Huttner, A., Hatz, C., van den Dobbelsteen, G., Abbanat, D., Hornacek, A., Frolich, R., Dreyer, A.M., Martin, P., Davies, T., Fae, K., et al. (2017). Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet Infect Dis.

(56) References Cited

OTHER PUBLICATIONS

Ihssen, J., et al., Increased efficiency of Campylobacter jejuni N-oligosaccharyltransferase PglB by structure-guided engineering. Open Biol, 2015. 5(4).

Ihssen, J., et al., Production of glycoprotein vaccines in *Escherichia coli*. Microb Cell Fact, 2010. 9: p. 61.

Imberty, A. and A. Varrot, Microbial recognition of human cell surface glycoconjugates. Curr Opin Struct Biol, 2008. 18(5): p. 567-76.

Iwashkiw, J.A., et al., Exploiting the Campylobacter jejuni protein glycosylation system for glycoengineering vaccines and diagnostic tools directed against brucellosis. Microb Cell Fact, 2012. 11: p. 13.

Jansson, P.E., et al., Structural studies of the *Escherichia coli* O78 O-antigen polysaccharide. Carbohydr Res, 1987. 165(1): p. 87-92.

Jaroentomeechai, T., et al., A Pipeline for Studying and Engineering Single-Subunit Oligosaccharyltransferases. Methods Enzymol, 2017. 597: p. 55-81.

Jaroentomeechai, T., et al., Single-pot glycoprotein biosynthesis using a cell-free transcription-translation system enriched with glycosylation machinery. Nat Commun, 2018. 9(1): p. 2686.

Jervis, A.J., et al., Characterization of the structurally diverse N-linked glycans of *Campylobacter* species. J Bacteriol, 2012. 194(9): p. 2355-62.

Jewett, M.C. and J.R. Swartz, Mimicking the *Escherichia coli* cytoplasmic environment activates long-lived and efficient cell-free protein synthesis. Biotechnology and bioengineering, 2004. 86(1): p. 19-26.

Jin, C., Gibani, M.M., Moore, M., Juel, H.B., Jones, E., Meiring, J., Harris, V., Gardner, J., Nebykova, A., Kerridge, S. A., et al. (2017). Efficacy and immunogenicity of a Vi-tetanus toxoid conjugate vaccine in the prevention of typhoid fever using a controlled human infection model of *Salmonella typhi*: a randomised controlled, phase 2b trial. Lancet 390, 2472-2480.

Johnson, J.R. (1991). Virulence factors in *Escherichia coli* urinary tract infection. Clin Microbiol Rev 4, 80-128.

Kaiser, L., et al., Efficient cell-free production of olfactory receptors: detergent optimization, structure, and ligand binding analyses. Proc Natl Acad Sci U S A, 2008. 105(41): p. 15726-31.

Kalynych, S., R. Morona, and M. Cygler, Progress in understanding the assembly process of bacterial O-antigen. FEMS Microbiol Rev, 2014. 38(5): p. 1048-65.

Kampf, M.M., et al., In vivo production of a novel glycoconjugate vaccine against Shigella flexneri 2a in recombinant *Escherichia coli*: identification of stimulating factors for in vivo glycosylation. Microb Cell Fact, 2015. 14: p. 12.

Karim, A.S. and M.C. Jewett, A cell-free framework for rapid biosynthetic pathway prototyping and enzyme discovery. Metab Eng, 2016. 36: p. 116-126.

Kim, D.M., and Swartz, J.R. (2001). Regeneration of adenosine triphosphate from glycolytic intermediates for cell-free protein synthesis. Biotechnol Bioeng 74, 309-316.

Knapp, K.G., Goerke, A.R., and Swartz, J.R. (2007). Cell-free synthesis of proteins that require disulfide bonds using glucose as an energy source. Biotechnol Bioeng 97, 901-908.

Kowarik, M., et al., Definition of the bacterial N-glycosylation site consensus sequence. The EMBO Journal, 2006. 25 (9): p. 1957-1966.

Kubick, S., et al., In vitro synthesis of posttranslationally modified membrane proteins. Current Topics in Membranes, 2009. 63(2): p. 25-49.

Kumru, O.S., et al., Vaccine instability in the cold chain: mechanisms, analysis and formulation strategies. Biologicals, 2014. 42(5): p. 237-59.

Kwon, Y.- C. and M.C. Jewett, High-throughput preparation methods of crude extract for robust cell-free protein synthesis. Scientific Reports, 2015. 5: p. 8663.

L'vov, V.L., Shashkov, A.S., Dmitriev, B.A., Kochetkov, N.K., Jann, B., and Jann, K. (1984). Structural studies of the O- specific side chain of the lipopolysaccharide from Escherichia coli O:7. Carbohydr Res 126, 249-259.

Laine, R.A., The Information-Storing Potential of the Sugar Code. Glycosciences: Status and Perspectives, 1997: p. 1-14.

Lehle, L. and W. Tanner, Glycosyl transfer from dolichyl phosphate sugars to endogenous and exogenous glycoprotein acceptors in yeast. Eur J Biochem, 1978. 83(2): p. 563-70.

Lesinski, G.B. and M.A. Westerink, Novel vaccine strategies to T-independent antigens. J Microbiol Methods, 2001. 47 (2): p. 135-49.

Lian, Q., H. Cao, and F. Wang, The cost-efficiency realization in the Escherichia coli-based cell-free protein synthesis systems. Appl Biochem Biotechnol, 2014. 174(7): p. 2351-67.

Inton, D., et al., Identification of N-acetylgalactosamine-containing glycoproteins PEB3 and CgpA in Campylobacter ejuni. Mol Microbiol, 2002. 43(2): p. 497-508.

Lizak, C., et al., X-ray structure of a bacterial oligosaccharyltransferase. Nature, 2011. 474(7351): p. 350-355.

Lu, Y., J.P. Welsh, and J.R. Swartz, Production and stabilization of the trimeric influenza hemagglutinin stem domain for potentially broadly protective influenza vaccines. Proc Natl Acad Sci U S A, 2014. 111(1): p. 125-30.

U, Z., Madico, G., Roche, M.I., Wang, Q., Hui, J.H., Perkins, H.M., Zaia, J., Costello, C.E., and Sharon, J. (2012). Protective B-cell epitopes of Francisella tularensis O-polysaccharide in a mouse model of respiratory tularaemia. Immunology 136, 352-360.

Ydon, P., Zipursky, S., Tevi-Benissan, C., Djingarey, M.H., Gbedonou, P., Youssouf, B.O., and Zaffran, M. (2014). Economic benefits of keeping vaccines at ambient temperature during mass vaccination: the case of meningitis A vaccine in Chad. Bull World Health Organ 92, 86-92.

Ma, Z. and K. Vosseller, Cancer metabolism and elevated O-GlcNAc in oncogenic signaling. J Biol Chem, 2014. 289 (50): p. 34457-65.

Ma, Z., et al., Glycoconjugate vaccine containing Escherichia coli 0157:H7 O-antigen linked with maltose-binding protein elicits humoral and cellular responses. PLOS One, 2014. 9(8): p. e105215.

Marshall, L.E., Nelson, M., Davies, C.H., Whelan, A.O., Jenner, D.C., Moule, M.G., Denman, C., Cuccui, J., Atkins, T. P., Wren, B.W., et al. (2018). An O-antigen glycoconjugate vaccine produced using protein glycan coupling technology is protective in an inhalational rat model of tularemia. J Immunol Res 2018, 8087916.

Matthies, D., et al., Cell-free expression and assembly of ATP synthase. J Mol Biol, 2011. 413(3): p. 593-603.

Maue, A.C., F. Poly, and p. Guerry, A capsule conjugate vaccine approach to prevent diarrheal disease caused by Campylobacter jejuni. Hum Vaccin Immunother, 2014. 10(6): p. 1499-504.

Mescher, M.F. and J.L. Strominger, Purification and characterization of a prokaryotic glucoprotein from the cell envelope of Halobacterium salinarium. J Biol Chem, 1976. 251(7): p. 2005-14.

Murphy, T.W., Sheng, J., Naler, L.B., Feng, X., and Lu, C. (2019). On-chip manufacturing of synthetic proteins for point-of-care therapeutics. Microsyst Nanoeng 5, 13.

Murray, G.L., S.R. Attridge, and R. Morona, Altering the length of the lipopolysaccharide O antigen has an impact on the interaction of Salmonella enterica serovar Typhimurium with macrophages and complement. J Bacteriol, 2006. 188 (7): p. 2735-9.

Murray, G.L., S.R. Attridge, and R. Morona, Regulation of Salmonella typhimurium lipopolysaccharide O antigen chain ength is required for virulence; identification of FepE as a second Wzz. Mol Microbiol, 2003. 47(5): p. 1395-406.

Needham, B.D., et al., Modulating the innate immune response by combinatorial engineering of endotoxin. Proc. Natl. Acad. Sci. U. S. A., 2013. 110(4): p. 1464-9.

Neuberger, A., Carbohydrates in protein: The carbohydrate component of crystalline egg albumin. Biochem J, 1938. 32 (9): p. 1435-51.

Ng, p. P., et al., A vaccine directed to B cells and produced by cell-free protein synthesis generates potent antilymphoma immunity. Proc Natl Acad Sci U S A, 2012. 109(36): p. 14526-31.

Nirenberg, M.W. and J.H. Matthaei, The dependence of cell-free protein synthesis in E. coli upon naturally occurring or synthetic polyribonucleotides. Proc Natl Acad Sci U S A, 1961. 47: p. 1588-602.

(56) References Cited

OTHER PUBLICATIONS

Nothaft, H., et al., Study of free oligosaccharides derived from the bacterial N-glycosylation pathway. Proc Natl Acad Sci U S A, 2009. 106(35): p. 15019-24.
Abu-Qarn, M., J. Eichler, and N. Sharon, Not just for Eukarya anymore: protein glycosylation in Bacteria and Archaea. Curr Opin Struct Biol, 2008. 18(5): p. 544-50.
Adiga, R., Al-adhami, M., Andar, A., Borhani, S., Brown, S., Burgenson, D., Cooper, M.A., Deldari, S., Frey, D.D., Ge, X., et al. (2018). Point-of-care production of therapeutic proteins of good-manufacturing-practice quality. Nat Biomed Eng.
Albrecht, S., et al., Glycosylation as a marker for inflammatory arthritis. Cancer Biomark, 2014. 14(1): p. 17-28.
Anderson, P., Antibody responses to Haemophilus influenzae type b and diphtheria toxin induced by conjugates of oligosaccharides of the type b capsule with the nontoxic protein CRM197. Infect Immun, 1983. 39(1): p. 233-8.
Ashok, A., Brison, M., and LeTallec, Y. (2017). Improving cold chain systems: Challenges and solutions. Vaccine 35, 2217-2223.
Axford, J.S., Glycosylation and rheumatic disease. Biochim Biophys Acta, 1999. 1455(2-3): p. 219-29.
Bacon, D.J., et al., A phase-variable capsule is involved in virulence of Campylobacter jejuni 81-176. Mol Microbiol, 2001. 40(3): p. 769-77.
Baudoin, L. and T. Issad, O-GlcNAcylation and Inflammation: A Vast Territory to Explore. Front Endocrinol (Lausanne), 2014. 5: p. 235.
Bayburt, T.H., and Sligar, S.G. (2010). Membrane protein assembly into Nanodiscs. FEBS Lett 584, 1721-1727.
Bernhard, F. and Y. Tozawa, Cell-free expression-making a mark. Curr Opin Struct Biol, 2013. 23(3): p. 374-80.
Bhushan, R., Anthony, B.F., and Frasch, C.E. (1998). Estimation of group B *Streptococcus* type III polysaccharide-specific antibody concentrations in human sera is antigen dependent. Infect Immun 66, 5848-5853.
Bogaert, D., Hermans, P.W., Adrian, P.V., Rumke, H.C., and de Groot, R. (2004). Pneumococcal vaccines: an update on current strategies. Vaccine 22, 2209-2220.
Boles, K.S., Kannan, K., Gill, J., Felderman, M., Gouvis, H., Hubby, B., Kamrud, K.I., Venter, J.C., and Gibson, D.G. (2017). Digital-to-biological converter for on-demand production of biologics. Nat Biotechnol 35, 672-675.
Brito, L.A., and Singh, M. (2011). Acceptable levels of endotoxin in vaccine formulations during preclinical research. J Pharm Sci 100, 34-37.
Brodel, A.K., D.A. Wustenhagen, and S. Kubick, Cell-free protein synthesis systems derived from cultured Mammalian cells. Methods Mol Biol, 2015. 1261: p. 129-40.
Bundy, B.C., M.J. Franciszkowicz, and J.R. Swartz, *Escherichia coli*-based cell-free synthesis of virus-like particles. Biotechnol Bioeng, 2008. 100(1): p. 28-37.
Calhoun, K.A. and J.R. Swartz, An economical method for cell-free protein synthesis using glucose and nucleoside monophosphates. Biotechnol Prog, 2005. 21(4): p. 1146-53.
Calhoun, K.A. and J.R. Swartz, Energizing cell-free protein synthesis with glucose metabolism. Biotechnol Bioeng, 2005. 90(5): p. 606-13.
Carlson, E.D., et al., Cell-free protein synthesis: applications come of age. Biotechnol Adv, 2012. 30(5): p. 1185-94.
Caschera, F. and V. Noireaux, Synthesis of 2.3 mg/ml of protein with an all *Escherichia coli* cell-free transcription-translation system. Biochimie, 2014. 99: p. 162-8.
Casella, C.R., and Mitchell, T.C. (2008). Putting endotoxin to work for us: monophosphoryl lipid A as a safe and effective vaccine adjuvant. Cell Mol Life Sci 65, 3231-3240.
CDC (2019). CDC Vaccine Price List.
Celik, E., Ollis, A.A., Lasanajak, Y., Fisher, A.C., Gur, G., Smith, D.F., and DeLisa, M.P. (2015). Glycoarrays with engineered phages displaying structurally diverse oligosaccharides enable high-throughput detection of glycan-protein interactions. Biotechnol J 10, 199-209.
Chambers, D.A. and G. Zubay, The stimulatory effect of cyclic adenosine 3'5'-monophosphate on DNA-directed synthesis of beta-galactosidase in a cell-free system. Proc Natl Acad Sci U S A, 1969. 63(1): p. 118-22.
Chauhan, J.S., A. Rao, and G.P. Raghava, In silico platform for prediction of N-, O- and C-glycosites in eukaryotic protein sequences. PLoS One, 2013. 8(6): p. e67008.
Chen, D.J., Osterrieder, N., Metzger, S.M., Buckles, E., Doody, A.M., DeLisa, M.P., and Putnam, D. (2010). Delivery of foreign antigens by engineered outer membrane vesicle vaccines. Proc Natl Acad Sci U S A 107, 3099-3104.
Chen, L., et al., Outer membrane vesicles displaying engineered glycotopes elicit protective antibodies. Proc Natl Acad Sci U S A, 2016. 113(26): p. E3609-18.
Chen, M.M., K.J. Glover, and B. Imperiali, From peptide to protein: comparative analysis of the substrate specificity of N-linked glycosylation in C. jejuni. Biochemistry, 2007. 46(18): p. 5579-85.
Chong, S., Overview of cell-free protein synthesis: historic landmarks, commercial systems, and expanding applications. Curr Protoc Mol Biol, 2014. 108: p. 16 30 1-11.
Crowell, L.E., Lu, A.E., Love, K.R., Stockdale, A., Timmick, S.M., Wu, D., Wang, Y.A., Doherty, W., Bonnyman, A., Vecchiarello, N., et al. (2018). On-demand manufacturing of clinical-quality biopharmaceuticals. Nat Biotechnol.
Cuccui, J., et al., Exploitation of bacterial N-linked glycosylation to develop a novel recombinant glycoconjugate vaccine against Francisella tularensis. Open Biol, 2013. 3(5): p. 130002.
Daniels, M.A., K.A. Hogquist, and S.C. Jameson, Sweet 'n' sour: the impact of differential glycosylation on T cell responses. Nat Immunol, 2002. 3(10): p. 903-10.
Datsenko, K.A., and Wanner, B.L. (2000). One-step inactivation of chromosomal genes in Escherichia coli K-12 using PCR products. Proc Natl Acad Sci U S A 97, 6640-6645.
Dennis, D.T., et al., Tularemia as a biological weapon: medical and public health management. Jama, 2001. 285(21): 0. 2763-73.
Dube, D.H. and A.R. Bertozzi, Glycans in cancer and inflammation-potential for therapeutics and diagnostics. Nat Rev Drug Discov, 2005. 4: p. 477-88.
Dudley, Q.M., A.S. Karim, and M.C. Jewett, Cell-free metabolic engineering: Biomanufacturing beyond the cell. Biotechnology Journal, 2015. 10(1): p. 69-82.
Duerr, C.U., et al., O-antigen delays lipopolysaccharide recognition and impairs antibacterial host defense in murine Intestinal epithelial cells. PLOS Pathog, 2009. 5(9): p. e1000567.
Feldman, M.F., et al., Engineering N-linked protein glycosylation with diverse O antigen lipopolysaccharide structures In Escherichia coli. Proc Natl Acad Sci U S A, 2005. 102(8): p. 3016-21.
Fernandez, S., Palmer, D.R., Simmons, M., Sun, P., Bisbing, J., McClain, S., Mani, S., Burgess, T., Gunther, V., and Sun, W. (2007). Potential role for Toll-like receptor 4 in mediating Escherichia coli maltose-binding protein activation of dendritic cells. Infect Immun 75, 1359-1363.
Figueiredo, D., Turcotte, C., Frankel, G., Li, Y., Dolly, O., Wilkin, G., Marriott, D., Fairweather, N., and Dougan, G. (1995). Characterization of recombinant tetanus toxin derivatives suitable for vaccine development. Infect Immun 63, 8218-3221.
Fisher, A.C., et al., Production of secretory and extracellular N-linked glycoproteins in Escherichia coli. Appl Environ Microbiol, 2011. 77(3): p. 871-81.
Frasch, C.E. (2009). Preparation of bacterial polysaccharide-protein conjugates: analytical and manufacturing challenges. Vaccine 27, 6468-6470.
Fulop, M., et al., Role of antibody to lipopolysaccharide in protection against low- and high-virulence strains of Francisella tularensis. Vaccine, 2001. 19(31): p. 4465-72.
Garcia-Quintanilla, F., et al., Production of a recombinant vaccine candidate against Burkholderia pseudomallei exploiting the bacterial N-glycosylation machinery. Front Microbiol, 2014. 5: p. 381.

(56) References Cited

OTHER PUBLICATIONS

Gavel, Y. and G. von Heijne, Sequence differences between glycosylated and non-glycosylated Asn-X-Thr/Ser acceptor sites: implications for protein engineering. Protein Eng, 1990. 3(5): p. 433-42.

Glover, K.J., E. Weerapana, and B. Imperiali, In vitro assembly of the undecaprenylpyrophosphate-linked heptasaccharide for prokaryotic N-linked glycosylation. Proc Natl Acad Sci U S A, 2005. 102(40): p. 14255-9.

Glover, K.J., et al., Direct biochemical evidence for the utilization of UDP-bacillosamine by PglC, an essential glycosyl-1-phosphate transferase in the Campylobacter jejuni N-linked glycosylation pathway. Biochemistry, 2006. 45 (16): p. 5343-50.

Guarino, C. and M.P. DeLisa, A prokaryote-based cell-free translation system that efficiently synthesizes glycoproteins. Glycobiology, 2012. 22(5): p. 596-601.

Guerry, P., et al., Campylobacter polysaccharide capsules: virulence and vaccines. Front Cell Infect Microbiol, 2012. 2: p. 7.

Haghi, F., Peerayeh, S.N., Siadat, S.D., and Montajabiniat, M. (2011). Cloning, expression and purification of outer membrane protein PorA of Neisseria meningitidis serogroup B. J Infect Dev Ctries 5, 856-862.

\* cited by examiner (A) →4)-α-D-GalNAcAN-(1 → 4)-α-D-GalNAcAN-(1 → 3)-β-D-QuiNAc-(1 → 2)-β-D-Qui4NFm-(1 →

(B) →3)-β-D-GlcNAc-(1 → 4)-β-D-GlcNAc-(1 → 4)-β-D-Man-(1 → 4)-β-D-Man-α1 →

__US 12,365,930 B2__

SEQUENCE LISTING

```
Sequence total quantity: 6
SEQ ID NO: 1                moltype = DNA   length = 1122
FEATURE                     Location/Qualifiers
source                      1..1122
                            mol_type = genomic DNA
                            organism = Escherichia coli
SEQUENCE: 1
atgtcaaaag tcgctctcat caccggtgta accggacaag acggttctta cctggcagag   60
tttctgctgg aaaaaggtta cgaggtgcat ggtattaagc gtcgcgcatc gtcattcaac  120
accgagcgcg tggatcacat ttatcaggat ccgcacacct gcaacccgaa attccatctg  180
cattatggcg acctgagtga tacctctaac ctgacgcgca ttttgcgtga agtacagccg  240
gatgaagtgt acaacctggg cgcaatgagc cacgttgcgg tctcttttga gtcaccagaa  300
tataccgctg acgtcgacgc gatgggtacg ctgcgcctgc tggaggcgat ccgcttcctc  360
ggtctggaaa agaaaactcg tttctatcag gcttccacct tgaactgta tggtctggtg   420
caggaaattc cgcagaaaga gaccacgccg ttctacccga gatctccgta tgccgtcgca  480
aaactgtacg cctactggat caccgttaac taccgtgaat cctacggcat gtacgcctgt  540
aacgaattc tcttcaacca tgaatccccg cgccgcggcg aaaccttcgt tacccgcaaa   600
atcacccgcg caatcgccaa catcgcccag ggctgagagt cgtgcctgta cctcggcaat  660
atggattccc tgcgtgactg gggccacgcc aaagactacg taaaaatgca gtggatgatg  720
ctgcagcagg aacagccgga agatttcgtt atcgcgaccg gcgttcagta ctccgtgcgt  780
cagttcgtgg aaatggcggc agcacagctg ggcatcaaac tgcgctttga aggcacgggc  840
gttgaagaga agggcattgt ggtttccgtc accgggcatg acgcgccggg cgttaaaccg  900
ggtgatgtga ttatcgctgt tgacccgcgt tacttccgtc cggctgaagt tgaaacgctg  960
ctcggcgacc cgaccaaagc gcacgaaaaa ctgggctgga aaccggaaat cacccctcaga 1020
gagatggtgt ctgaaatggt ggctaatgac ctcgaagcgg cgaaaaaaca ctctctgctg 1080
aaatctcacg gctacgacgt ggcgatcgcg ctggagtcat aa                    1122

SEQ ID NO: 2                moltype = AA   length = 373
FEATURE                     Location/Qualifiers
source                      1..373
                            mol_type = protein
                            organism = Escherichia coli
SEQUENCE: 2
MSKVALITGV TGQDGSYLAE FLLEKGYEVH GIKRRASSFN TERVDHIYQD PHTCNPKFHL   60
HYGDLSDTSN LTRILREVQP DEVYNLGAMS HVAVSFESPE YTADVDAMGT LRLLEAIRFL  120
GLEKKTRFYQ ASTSELYGLV QEIPQKETTP FYPRSPYAVA KLYAYWITVN YRESYGMYAC  180
NGILFNHESP RRGETFVTRK ITRAIANIAQ GLESCLYLGN MDSLRDWGHA KDYVKMQWMM  240
LQQEQPEDFV IATGVQYSVR QFVEMAAAQL GIKLRFEGTG VEEKGIVVSV TGHDAPGVKP  300
GDVIIAVDPR YFRPAEVETL LGDPTKAHEK LGWKPEITLR EMVSEMVAND LEAAKKHSLL  360
KSHGYDVAIA LES                                                    373

SEQ ID NO: 3                moltype = DNA   length = 1260
FEATURE                     Location/Qualifiers
source                      1..1260
                            mol_type = genomic DNA
                            organism = Escherichia coli
SEQUENCE: 3
atgctaacat cctttaaact tcattcattg aaaccttaca ctctgaaatc atcaatgatt   60
ttagagataa taacttatat attatgtttt ttttcaatga taattgcatt cgtcgataat  120
actttcagca taaaaatata taatatcact gctatagttt gcttattgtc actaattta   180
cgtggcagac aagaaaatta aatataaaa accttattc ttccccttc tatattttta    240
ataggcttgc ttgatttaat ttggtattct gcgtttaaga tagataattc gccatttcgt  300
gctacttacc atagtatt aaatactgcc aaaatattta tatttggttc tttatttgtt   360
ttcttgacac taactagcca gctaaaatca aaaaaagaga gtgtattata cactttgtat  420
tctctgtcat ttctaattgc tggatatgca atgtatatta atagcattca tgaaaatgac  480
cgcatttctt ttggtgtagg aacggcaaca ggagcagcat attcaacaat gctaataggg  540
atagttagtg gcgttgcgat tctttatact aagaaaaatc atccttttt attttattta  600
aatagttgcg cggtactta tgttctggcc ctaacacaaa ccagagcaac cctactcctg  660
ttccctataa tttgtgttgc tgcattaata gcttattata taaatcacc caagaaattc   720
acttcctcta ttgttctact aattgctata ttagctagca ttgttattat atttaataaa  780
ccaatacaga atcgctataa tgaagcatta aatgacttaa gcagttatac caatgctaat  840
agtgttactt cccctaggtgc aagactggca atgtacgaaa ttggtttaaa tatattcata  900
aagtcacctt tttcatttag atcagcagag tcacgcgctg aaagtatgaa tttgttagtt  960
gcagaacaca taggctaag aggggcattg gagttttcta acgtacatct acataatgag 1020
ataattgaag cagggtcact gaaaggtctg atgggaattt tttccacact tttcctctat 1080
ttttcactat tttatatagc atataaaaaa cgagctttgg gttgttgat attaacgctt   1140
ggcattgtgg ggattggact cagtgatgtg atcatatggg cacgcagcat tccaattatc 1200
attatatccg ctatagtcct cttactcgtc attaataatc gtaacaatac aattaattaa 1260

SEQ ID NO: 4                moltype = AA   length = 419
FEATURE                     Location/Qualifiers
source                      1..419
                            mol_type = protein
                            organism = Escherichia coli
SEQUENCE: 4
MLTSFKLHSL KPYTLKSSMI LEIITYILCF FSMIIAFVDN TFSIKIYNIT AIVCLLSLIL   60
RGRQENYNIK NLILPLSIFL IGLLDLIWYS AFKVDNSPFR ATYHSYLNTA KIFIFGSFIV  120
FLTLTSQLKS KKESVLYTLY SLSFLIAGYA MYINSIHEND RISFGVGTAT GAAYSTMLIG  180
```

-continued

```
IVSGVAILYT KKNHPFLFLL NSCAVLYVLA LTQTRATLLL FPIICVAALI AYYNKSPKKF  240
TSSIVLLIAI LASIVIIFNK PIQNRYNEAL NDLNSYTNAN SVTSLGARLA MYEIGLNIFI  300
KSPFSFRSAE SRAESMNLLV AEHNRLRGAL EFSNVHLHNE IIEAGSLKGL MGIFSTLFLY  360
FSLFYIAYKK RALGLLILTL GIVGIGLSDV IIWARSIPII IISAIVLLLV INNRNNTIN   419

SEQ ID NO: 5              moltype = DNA  length = 2142
FEATURE                   Location/Qualifiers
source                    1..2142
                          mol_type = genomic DNA
                          organism = Campylobacter jejuni
SEQUENCE: 5
atgttgaaaa aagagtattt aaaaaaccct tatttagttt tgtttgcgat gattgtatta    60
gcttatgttt ttagtgtatt ttgcaggttt tattgggttt ggtgggcaag tgagtttaac   120
gagtatttt tcaataatca attaatgatc atttcaaacg atggctatgc ttttgctgag   180
ggcgcaagag atatgatagc aggttttcat cagcctaatg atttgagtta ttatggatct   240
tctttatcta cgcttactta ttggctttat aaaatcacac cttttctttt tgaaagtatc   300
attttatata tgagtacttt tttatcttct tggtggtga ttcctattat tttactagct    360
aatgaataca aacgcccttt aatgggcttt gtagctgctc ttttagcaag tgtagcaaac   420
agttattata atcgcactat gagtgggtat tatgatacgg atatgctggt aattgtttta   480
cctatgttta tttatttt tatggtaaga atgattttaa aaaagactt tttttcattg     540
attgccttgc cattatttat aggaatttat ctttggtggt atccttcaag ttatacttta   600
aatgtagctt taattggact ttttttaatt tatacactta ttttcatag aaaagaaag    660
attttttata tagctgtgat tttgtcttcc cttactcttt caaatatagc atggttttat   720
caaagtgcca ttatagtaat acttttgct ttatttgctt tagagcaaaa acgcttaaat    780
tttatgatta taggaatttt aggtagtgca actttgatat ttttgatttt aagtggtggg   840
gttgatccca tactttatca gcttaaattt tatattttta gaagcgatga aagtgcgaat   900
taacacagg gctttatgta ttttaatgtt aatcaaacca tacaagaagt tgaaaatgta   960
gattttagcg aatttatgcg aagaattagt ggtagtgaaa ttgttttctt gttttctttg  1020
tttggttttg tatggctttt gagaaaacat aaaagtatga ttatggcttt acctatattg  1080
gtgcttgggt ttttagcctt aaaaggagga cttagattta ccatttattc tgtacctgta  1140
atggctttag gatttggtt tttattgagc gagtttaagg ctatattggt taaaaaatat   1200
agccaattaa cttcaaatgt tgtattgtt tttgcaacta ttttgacttt ggctccagta   1260
tttatccata tttacaacta taagcgcca acagttttt ctcaaaatga agcatcatta    1320
ttaaatcaat taaaaatat agccaataga gaagattatg tggtaacttg gtgggattat   1380
ggttatcctg tgcgttatta tagcgatgtg aaaactttag tagatggtgg aaagcattta  1440
ggtaaggata attttttccc ttcttttct ttaagtaaag atgaacaagc tgcagctaat   1500
atggcaagac ttagtgtaga atatacgaaa aaagcttttt atgctccgca aaatgatatt  1560
ttaaaatcag acattttaca agccatgatg aaagattata tcaaagcaa tgtggattta   1620
tttctagctt cattatcaaa acctgatttt aaaatcgata caccaaaac tcgtgatatt   1680
tatcttata tgcccgctag aatgtctttg attttttcta cggtggctag ttttttcttt  1740
attaatttag atacaggagt tttggataaa cctttaccct ttagcacagc ttatccactt  1800
gatgttaaaa atggagaaat ttatcttagc aacggagtgg ttaagcga tgatttaga     1860
agtttaaaa taggtgataa tgtggtttct gtaaatagta tcgtagagat taattctatt   1920
aaacaaggtg aatacaaat cactccaatc gatgataagg ctcagtttta tatttttat   1980
ttaaaggata gtgctattcc ttacgcacaa tttattttaa tggataaaac catgtttaat   2040
agtgcttatg tgcaaatgtt ttttttggga aattatgata agaattatt tgacttggtg   2100
attaattcta gagatgctaa agtttttaaa cttaaaattt aa                     2142

SEQ ID NO: 6              moltype = AA  length = 713
FEATURE                   Location/Qualifiers
source                    1..713
                          mol_type = protein
                          organism = Campylobacter jejuni
SEQUENCE: 6
MLKKEYLKNP YLVLFAMIVL AYVFSVFCRF YWVWWASEFN EYFFNNQLMI ISNDGYAFAE    60
GARDMIAGFH QPNDLSYYGS SLSTLTYWLY KITPFSFESI ILYMSTFLSS LVVIPIILLA   120
NEYKRPLMGF VAALLASVAN SYYNRTMSGY YDTDMLVIVL PMFILFFMVR MILKKDFFSL   180
IALPLFIGIY LWWYPSSYTL NVALIGLFLI YTLIFHRKEK IFYIAVILSS LTLSNIAWFY   240
QSAIIVILFA LFALEQKRLN FMIIGILGSA TLIFLILSGG VDPILYQLKF YIFRSDESAN   300
LTQGFMYFNV NQTIQEVENV DFSEFMRRIS GSEIVFLFSL FGFVWLLRKH KSMIMALPIL   360
VLGFLALKGG LRFTIYSVPV MALGFGFLLS EFKAILVKKY SQLTSNVCIV FATILTLAPV   420
FIHIYNYKAP TVFSQNEASL LNQLKNIANR EDYVVTWWDY GYPVRYYSDV KTLVDGGKHL   480
GKDNFFPSFS LSKDEQAAAN MARLSVEYTE KSFYAPQNDI LKSDILQAMM KDYNQSNVDL   540
FLASLSKPDF KIDTPKTRDI YLYMPARMSL IFSTVASFSF INLDTGVLDK PFTFSTAYPL   600
DVKNGEIYLS NGVVLSDDFR SFKIGDNVVS VNSIVEINSI KQGEYKITPI DDKAQFYIFY   660
LKDSAIPYAQ FILMDKTMFN SAYVQMFFLG NYDKNLFDLV INSRDAKVFK LKI          713
```

METHOD FOR RAPID IN VITRO SYNTHESIS OF GLYCOPROTEINS VIA RECOMBINANT PRODUCTION OF N-GLYCOSYLATED PROTEINS IN PROKARYOTIC CELL LYSATES

CROSS-REFERENCE TO RELATED PATENT APPLICATIONS

The present application is a continuation of U.S. application Ser. No. 17/077,354, filed Oct. 22, 2022, which is a continuation of U.S. patent application Ser. No. 15/650,127, filed Jul. 14, 2017, now U.S. Pat. No. 10,829,795, which claims the benefit of priority under 35 U.S.C. § 119(e) to U.S. Provisional Patent Application 62/362,327, filed on Jul. 14, 2016. The content of each of the above-referenced applications is incorporated herein by reference in its entirety.

STATEMENT REGARDING FEDERALLY SPONSORED RESEARCH OR DEVELOPMENT

This invention was made with government support under MCB1413563 awarded by the National Science Foundation. The government has certain rights in the invention.

SEQUENCE LISTING

A Sequence Listing accompanies this application and is submitted as an XML file of the sequence listing named "702581_02268_Sequence_Listing.xml" which is 12,398 bytes in size and was created on May 26, 2023. The sequence listing is electronically submitted via Patent Center with the application and is incorporated herein by reference in its entirety.

BACKGROUND

The field of the invention relates to in vitro synthesis of N-glycosylated protein in prokaryotic cell lysates. In particular, the field of the invention relates to the use of N-glycosylated proteins synthesized in vitro in prokaryotic cell lysates as vaccine conjugates against pathogens such as bacteria.

Conjugate vaccines are among the safest and most effective methods for prevention of life-threatening bacterial infections. Bioconjugate vaccines are a type of conjugate vaccine produced via protein glycan coupling technology (PGCT), in which polysaccharide antigens are conjugated via N-glycosylation to recombinant carrier proteins using a bacterial oligosaccharyltransferase (OST) in living *Escherichia coli* cells. Bioconjugate vaccines have the potential to greatly reduce the time and cost required to produce antibacterial vaccines. However, PGCT is limited by: i) the length of in vivo process development timelines; and ii) the fact that FDA-approved carrier proteins, such as the toxins from *Clostridium tetani* and *Corynebacterium diphtheriae*, have not yet been demonstrated to be compatible with N-linked glycosylation in living *E. coli*. Here, we have applied cell-free glycoprotein synthesis (CFGpS) technology to enable rapid in vitro production of bioconjugate vaccines against pathogenic strains of *Escherichia coli* and *Franciscella tularensis* in reactions lasting 20 hours. Due to the modular nature of the CFGpS system, this cell-free strategy could be easily applied to produce bioconjugates using FDA-approved carrier proteins or additional vaccines against pathogenic bacteria whose surface antigen gene clusters are known. We further show that this system can be lyophilized and retain bioconjugate synthesis capability, demonstrating the potential for on-demand vaccine production and development in resource-poor settings. This work represents the first demonstration of bioconjugate vaccine production in *E. coli* lysates and has promising applications as a portable prototyping or production platform for antibacterial vaccine candidates.

SUMMARY

Disclosed are methods, systems, components, and compositions for cell-free synthesis of glycosylated proteins. The glycosylated proteins may be utilized in vaccines, including anti-bacterial vaccines. The glycosylated proteins may include a bacterial polysaccharide conjugated to a carrier, which may be utilized to generate an immune response in an immunized host against the polysaccharide conjugated to the carrier. The glycosylated proteins may be synthesized in cell-free glycoprotein synthesis (CFGpS) systems using prokaryote cell lysates that are enriched in components for glycoprotein synthesis such as oligosaccharyltransferases (OSTs) and lipid-linked oligosaccharides (LLOs) including OSTs and LLOs associated with synthesis of bacterial O-antigens. As such, the prokaryote cell lysates may be prepared from recombinant prokaryotes that have been engineered to express heterologous OSTs and/or that have been engineered to express heterologous glycan synthesis pathways for production of LLOs. The disclosed lysates may be described as modular and may be combined to prepare glycosylated proteins in the disclosed CFGpS systems.

Figure 1:
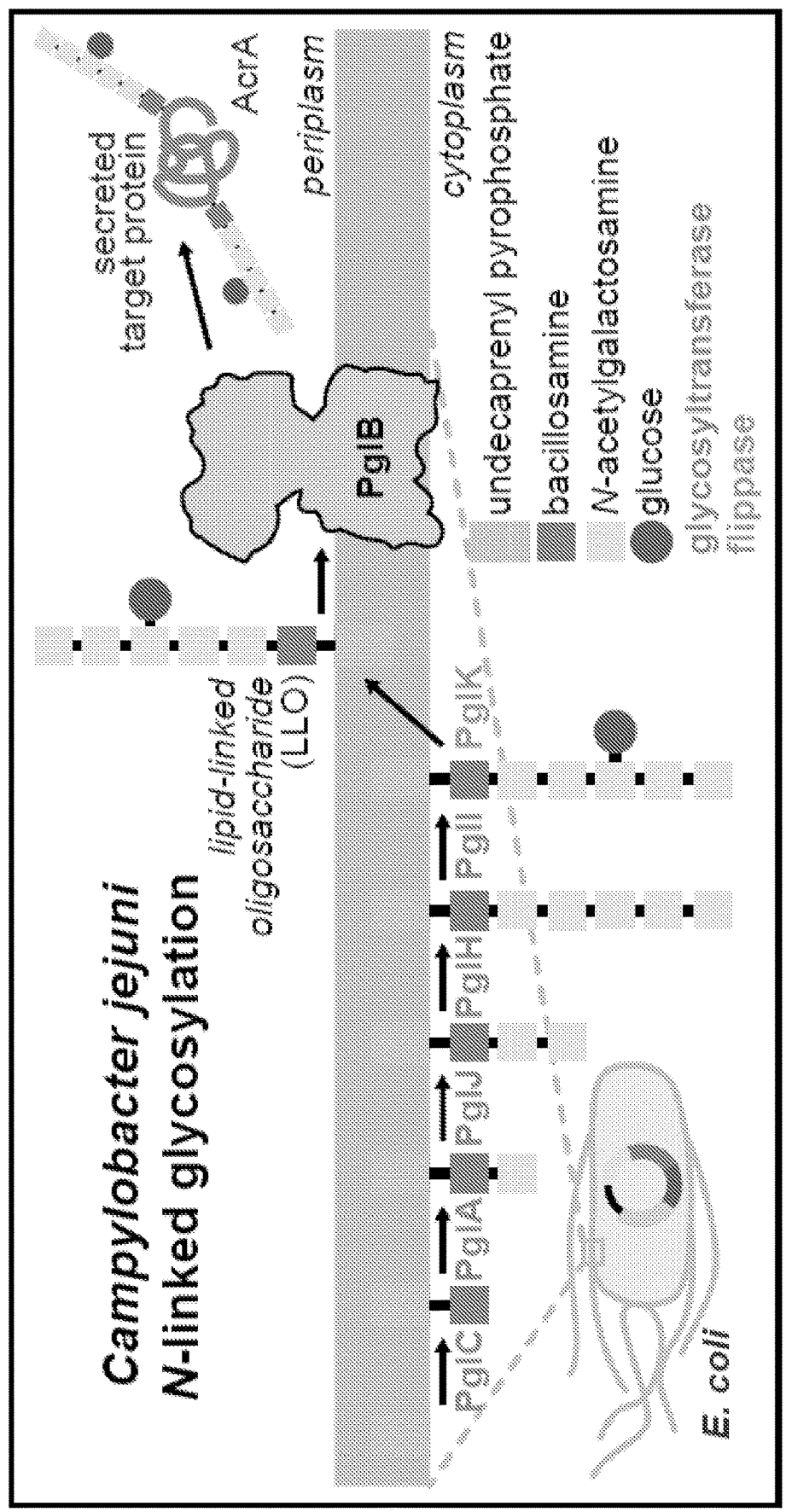
FIG. 1. Schematic depicting function of *C. jejuni* N-linked glycosylation pathway expressed in *E. coli* as adapted from Guarino C., and DeLisa M. P., Glycobiology, 2012 May 22(5):596-601, the content of which is incorporated herein by reference in its entirety.

His. The EcO78-PS is covalently attached to sfGFP-21-DQNAT and MBP-4×DQNAT when both the CjOST and EcO78LLO lysate are present in the CFGpS reaction, indicated by the ladder-like pattern observed in the Western blot assay (lanes 2, 4). The bioconjugates were also cross-reactive with a commercial antiserum against the *E. coli* O78 strain (data not shown). These results demonstrate the modularity of LLOs in mixed lysate CFGpS and the potential of CFGpS technology for rapid synthesis of antibacterial vaccines. Abbreviations: CLM24 pSF CjOST; FtLLO lysate: CLM24 pGAB2; α-FtO antigen: FB11 mAb specific for *F. tularensis* O-antigen glycan.

FIG. 5. Freeze-dried CFGpS reactions for point-of-use vaccine manufacturing. (A) Scheme for portable bioconjugate production and distribution in resource-limited settings. (B) Lyophilized CFGpS reactions retain bioconjugate synthesis activity. CFGpS reactions were prepared containing either CjOST lysate or FtLLO lysate alone, or a mixture of both CjOST and FtLLO lysates. These reactions were then lyophilized and reconstituted with 15 μL nuclease-free water. Pre-mixed reactions (lanes 1, 2, 5, 6) were run directly following reconstitution, while reactions containing CjOST lysate or FtLLO lysate alone were mixed following reconstitution (lanes 3, 4, 7). The FtO-PS is attached to the target protein when the DQNAT sequon is synthesized and both CjOST lysate or FtLLO lysate are present in the reaction (lanes 2, 4, 6, 7). Bioconjugate synthesis capability is preserved following lyophilization, demonstrating the potential of CFGpS for portable bioconjugate production and distribution in resource-poor areas. Abbreviations: CjOST lysate: CLM24 pSF CjOST; FtLLO lysate: CLM24 pGAB2; α-FtO antigen: FB11 mAb specific for *F. tularensis* O-antigen glycan.

FIG. 6. Structures of O-antigens produced in selectively enriched S30 lysates. (A) Structure of the *F. tularensis* Schu S4 O-antigen (B) Structure of the enterotoxigenic *E. coli* O78 antigen.

DETAILED DESCRIPTION

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms “a,” “an,” and “the” include plural forms unless the context clearly dictates otherwise. For example, the term “a gene” or “an oligosaccharide” should be interpreted to mean “one or more genes” and “one or more oligosaccharides,” respectively, unless the context clearly dictates otherwise. As used herein, the term “plurality” means “two or more.”

As used herein, “about”, “approximately,” “substantially,” and “significantly” will be understood by persons of ordinary skill in the art and will vary to some extent on the context in which they are used. If there are uses of the term which are not clear to persons of ordinary skill in the art given the context in which it is used, “about” and “approximately” will mean up to plus or minus 10% of the particular term and “substantially” and “significantly” will mean more than plus or minus 10% of the particular term.

As used herein, the terms “include” and “including” have the same meaning as the terms “comprise” and “comprising.” The terms “comprise” and “comprising” should be interpreted as being “open” transitional terms that permit the inclusion of additional components further to those components recited in the claims. The terms “consist” and “consisting of” should be interpreted as being “closed” transitional terms that do not permit the inclusion of additional components other than the components recited in the claims. The term “consisting essentially of” should be interpreted to be partially closed and allowing the inclusion only of additional components that do not fundamentally alter the nature of the claimed subject matter.

The phrase “such as” should be interpreted as “for example, including.” Moreover the use of any and all exemplary language, including but not limited to “such as”, is intended merely to better illuminate the invention and does not pose a limitation on the scope of the invention unless otherwise claimed.

Furthermore, in those instances where a convention analogous to “at least one of A, B and C, etc.” is used, in general such a construction is intended in the sense of one having ordinary skill in the art would understand the convention (e.g., “a system having at least one of A, B and C” would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase “A or B” will be understood to include the possibilities of “A” or ‘B or “A and B.”

All language such as “up to,” “at least,” “greater than,” “less than,” and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb “may” refers to the preferred use or selection of one or more options or choices among the several described embodiments or features contained within the same. Where no options or choices are disclosed regarding a particular embodiment or feature contained in the same, the modal verb “may” refers to an affirmative act regarding how to make or use and aspect of a described embodiment or feature contained in the same, or a definitive decision to use a specific skill regarding a described embodiment or feature contained in the same. In this latter context, the modal verb “may” has the same meaning and connotation as the auxiliary verb “can.”

As used herein, the terms “bind,” “binding,” “interact,” “interacting,” “occupy” and “occupying” refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly$(A)_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

As utilized herein, a "deletion" means the removal of one or more nucleotides relative to the native polynucleotide sequence. The engineered strains that are disclosed herein may include a deletion in one or more genes (e.g., a deletion in gmd and/or a deletion in waaL). Preferably, a deletion results in a non-functional gene product. As utilized herein, an "insertion" means the addition of one or more nucleotides to the native polynucleotide sequence. The engineered strains that are disclosed herein may include an insertion in one or more genes (e.g., an insertion in gmd and/or an insertion in waaL). Preferably, a deletion results in a non-functional gene product. As utilized herein, a "substitution" means replacement of a nucleotide of a native polynucleotide sequence with a nucleotide that is not native to the polynucleotide sequence. The engineered strains that are disclosed herein may include a substitution in one or more genes (e.g., a substitution in gmd and/or a substitution in waaL). Preferably, a substitution results in a non-functional gene product, for example, where the substitution introduces a premature stop codon (e.g., TAA, TAG, or TGA) in the coding sequence of the gene product. In some embodiments, the engineered strains that are disclosed herein may include two or more substitutions where the substitutions introduce multiple premature stop codons (e.g., TAATAA, TAGTAG, or TGATGA).

In some embodiments, the engineered strains disclosed herein may be engineered to include and express one or more heterologous genes. As would be understood in the art, a heterologous gene is a gene that is not naturally present in the engineered strain as the strain occurs in nature. A gene that is heterologous to *E. coli* is a gene that does not occur in *E. coli* and may be a gene that occurs naturally in another microorganism (e.g. a gene from *C. jejuni*) or a gene that does not occur naturally in any other known microorganism (i.e., an artificial gene).

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited to, a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phosphono, phosphine, heterocyclic, enone, imine, aldehyde, hydroxylamine, keto, or amino substituted amino acid, or a combination thereof, an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Reference may be made herein to peptides, polypeptides, proteins and variants thereof. Variants as contemplated herein may have an amino acid sequence that includes conservative amino acid substitutions relative to a reference amino acid sequence. For example, a variant peptide, polypeptide, or protein as contemplated herein may include conservative amino acid substitutions and/or non-conservative amino acid substitutions relative to a reference peptide, polypeptide, or protein. "Conservative amino acid substitutions" are those substitutions that are predicted to interfere least with the properties of the reference peptide, polypeptide, or protein, and "non-conservative amino acid substitution" are those substitution that are predicted to interfere most with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

TABLE 1

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain.

Variants comprising deletions relative to a reference amino acid sequence of peptide, polypeptide, or protein are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants comprising fragment of a reference amino acid sequence of a peptide, polypeptide, or protein are contemplated herein. A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide.

Variants comprising insertions or additions relative to a reference amino acid sequence of a peptide, polypeptide, or protein are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. A "fusion protein" refers to a protein formed by the fusion of at least one peptide, polypeptide, or protein or variant thereof as disclosed herein to at least one heterologous protein peptide, polypeptide, or protein (or fragment or variant thereof). The heterologous protein(s) may be fused at the N-terminus, the C-terminus, or both termini of the peptides or variants thereof.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide (e.g., glycosylase activity or other activity). "Substantially isolated or purified" amino acid sequences are contemplated herein. The term "substantially isolated or purified" refers to amino acid sequences that are removed from their natural environment, and are at least 60% free, preferably at least 75% free, and more preferably at least 90% free, even more preferably at least 95% free from other components with which they are naturally associated.

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Cell-Free Protein Synthesis (CFPS)

The strains and systems disclosed herein may be applied to cell-free protein synthesis methods as known in the art. See, for example, U.S. Pat. Nos. 4,496,538; 4,727,136; 5,478,730; 5,556,769; 5,623,057; 5,665,563; 5,679,352; 6,168,931; 6,248,334; 6,531,131; 6,869,774; 6,994,986; 7,118,883; 7,189,528; 7,338,789; 7,387,884; 7,399,610; 8,703,471; and 8,999,668. See also U.S. Published Application Nos. 2015-0259757, 2014-0295492, 2014-0255987, 2014-0045267, 2012-0171720, 2008-0138857, 2007-0154983, 2005-0054044, and 2004-0209321. See also U.S Published Application Nos. 2005-0170452; 2006-0211085; 2006-0234345; 2006-0252672; 2006-0257399; 2006-0286637; 2007-0026485; 2007-0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or glycosylation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for transcription, translation, and/or glycosylation, e.g., potassium glutamate, ammonium chloride and the like. Physiological cytoplasmic salt conditions are well-known to those of skill in the art.

The strains and systems disclosed herein may be applied to cell-free protein methods in order to prepare glycosylated macromolecules (e.g., glycosylated peptides, glycosylated proteins, and glycosylated lipids). Glycosylated proteins that may be prepared using the disclosed strains and systems may include proteins having N-linked glycosylation (i.e., glycans attached to nitrogen of asparagine and/or arginine side-chains) and/or O-linked glycosylation (i.e., glycans attached to the hydroxyl oxygen of serine, threonine, tyrosine, hydroxylysine, and/or hydroxyproline). Glycosylated lipids may include O-linked glycans via an oxygen atom, such as ceramide.

The glycosylated macromolecules disclosed herein may include unbranched and/or branched sugar chains composed of monomers as known in the art such as, but not limited to, glucose (e.g., β-D-glucose), galactose (e.g., β-D-galactose), mannose (e.g., β-D-mannose), fucose (e.g., α-L-fucose), N-acetyl-glucosamine (GlcNAc), N-acetyl-galactosamine (GalNAc), neuraminic acid, N-acetylneuraminic acid (i.e., sialic acid), and xylose, which may be attached to the glycosylated macromolecule, growing glycan chain, or donor molecule (e.g., a donor lipid and/or a donor nucleotide) via respective glycosyltransferases (e.g., oligosaccharyltransferases, GlcNAc transferases, GalNAc transferases, galactosyltransferases, and sialyltransferases). The glycosylated macromolecules disclosed herein may include glycans as known in the art.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

Cell-Free Glycoprotein Synthesis (CFGpS) in Prokaryotic Cell Lysates Enriched with Components for Glycosylation Disclosed are compositions and methods for performing cell-free glycoprotein synthesis (CFGpS). In some embodiments, the composition and methods include or utilize prokaryotic cell lysates enriched with components for glycosylation and prepared from genetically modified strains of prokaryotes.

In some embodiments, the genetically modified prokaryote is a genetically modified strain of *Escherichia coli* or any other prokaryote suitable for preparing a lysate for CFGpS. Optionally, the modified strain of *Escherichia coli* is derived from rEc.C321. Preferably, the modified strain includes genomic modifications (e.g., deletions of genes rendering the genes inoperable) that preferably result in lysates capable of high-yielding cell-free protein synthesis. Also, preferably, the modified strain includes genomic modification (e.g., deletions of genes rendering the genes inoperable) that preferably result in lysates comprising sugar precursors for glycosylation at relatively high concentrations (e.g., in comparison to a strain not having the genomic modification). In some embodiments, a lysate prepared from the modified strain comprises sugar precursors at a concentration that is at least 20%, 30%, 40%, 50%, 60%, 70%, 80%, 90%, 100%, 150%, 200%, or higher than a lysate prepared from a strain that is not modified.

In some embodiments, the modified strain includes a modification that results in an increase in the concentration of a monosaccharide utilized in glycosylation (e.g., glucose, mannose, N-acetyl-glucosamine (GlcNAc), N-acetyl-galactosamine (GalNAc), galactose, sialic acid, neuraminic acid, fucose). As such, the modification may inactivate an enzyme that metabolizes a monosaccharide or polysaccharide utilized in glycosylation. In some embodiments, the modification inactivates a dehydratase or carbon-oxygen lyase enzyme (EC 4.2) (e.g., via a deletion of at least a portion of the gene encoding the enzyme). In particular, the modification may inactivate a GDP-mannose 4,6-dehydratase (EC 4.2.1.47). When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2.

In some embodiments, the modified strain includes a modification that inactivates an enzyme that is utilized in the glycosyltransferase pathway. In some embodiments, the modification inactivates an oligosaccharide ligase enzyme (e.g., via a deletion of at least a portion of the gene encoding the enzyme). In particular, the modification may inactivate an O-antigen ligase that optionally conjugates an O-antigen to a lipid A core oligosaccharide. The modification may include an inactivating modification in the waaL gene (e.g., via a deletion of at least a portion of the waaL gene). The sequence of the *E. coli* waaL gene is provided herein as SEQ ID NO:3 and the amino acid sequence of *E. coli* O-antigen ligase is provided as SEQ ID NO:4

In some embodiments, the modified strain includes a modification that inactivates a dehydratase or carbon-oxygen lyase enzyme (e.g., via a deletion of at least a portion of the gene encoding the enzyme) and also the modified strain includes a modification that inactivates an oligosaccharide ligase enzyme (e.g., via a deletion of at least a portion of the gene encoding the enzyme). The modified strain may include an inactivation or deletion of both gmd and waaL.

In some embodiments, the modified strain may be modified to express one or more orthogonal or heterologous genes. In particular, the modified strain may be genetically modified to express an orthogonal or heterologous gene that is associated with glycoprotein synthesis such as a glycosyltransferase (GT) which is involved in the lipid-linked oligosaccharide (LLO) pathway. In some embodiments, the modified strain may be modified to express an orthogonal or heterologous oligosaccharyltransferase (EC 2.4.1.119) (OST). Oligosaccharyltransferases or OSTs are enzymes that transfer oligosaccharides from lipids to proteins.

In particular, the modified strain may be genetically modified to express an orthogonal or heterologous gene in a glycosylation system (e.g., an N-linked glycosylation system and/or an O-linked glycosylation system). The N-linked glycosylation system of *Campylobacter jejuni* has been transferred to *E. coli*. (See Wacker et al., "N-linked glycosylation in *Campylobacter jejuni* and its functional transfer into *E. coli*," Science 2002 Nov. 29; 298(5599):1790-3, the content of which is incorporated herein by reference in its entirety). In particular, the modified strain may be modified to express one or more genes of the pgl locus of *C. jejuni* or one or more genes of a homologous pgl locus. The genes of the pgl locus include pglG, pglF, pglE, wlaJ, pglD, pglC, pgA, pglB, pglJ, pglI, pglH, pglK, and gne, and are used to synthesize lipid-linked oligosaccharides (LLOs) and transfer the oligosaccharide moieties of the LLOs to a protein via an oligosaccharyltransferase.

Suitable orthogonal or heterologous oligosaccharyltransferases (OST) which may be expressed in the genetically modified strains may include *Campylobacter jejuni* oligosaccharyltransferase PglB. The gene for the *C. jejuni* OST is referred to as pglB, which sequence is provided as SEQ ID NO:5 and the amino acid sequence of *C. jejuni* PglB is provided as SEQ ID NO:6. PglB catalyzes transfer of an oligosaccharide to a D/E-Y-N-X-S/T motif (Y, X≠P) present on a protein.

Crude cell lysates may be prepared from the modified strains disclosed herein. The crude cell lysates may be prepared from different modified strains as disclosed herein and the crude cell lysates may be combined to prepare a mixed crude cell lysate. In some embodiments, one or more crude cell lysates may be prepared from one or more modified strains including a genomic modification (e.g., deletions of genes rendering the genes inoperable) that preferably result in lysates comprising sugar precursors for glycosylation at relatively high concentrations (e.g., in comparison to a strain not having the genomic modification). In some embodiments, one or more crude cell lysates may be prepared from one or more modified strains that have been modified to express one or more orthogonal or heterologous genes or gene clusters that are associated with glycoprotein synthesis. Preferably, the crude cell lysates or mixed crude cell lysates are enriched in glycosylation components, such as lipid-linked oligosaccharides (LLOs), glycosyltransferases (GTs), oligosaccharyltransferases (OSTs), or any combination thereof. More preferably, the crude cell lysates or mixed crude cell lysates are enriched in Man$_3$GlcNAc$_2$ LLOs representing the core eukaryotic glycan and/or Man$_3$GlcNAc$_4$Gal$_2$Neu$_5$Ac$_2$ LLOs representing the fully sialylated human glycan.

The disclosed crude cell lysates may be used in cell-free glycoprotein synthesis (CFGpS) systems to synthesize a variety of glycoproteins. The glycoproteins synthesized in the CFGpS systems may include prokaryotic glycoproteins and eukaryotic proteins, including human proteins. The CFGpS systems may be utilized in methods for synthesizing glycoproteins in vitro by performing the following steps using the crude cell lysates or mixtures of crude cell lysates disclosed herein: (a) performing cell-free transcription of a gene for a target glycoprotein; (b) performing cell-free translation; and (c) performing cell-free glycosylation. The methods may be performed in a single vessel or multiple vessels. Preferably, the steps of the synthesis method may be performed using a single reaction vessel. The disclosed methods may be used to synthesis a variety of glycoproteins, including prokaryotic glycoproteins and eukaryotic glycoproteins.

Bioconjugate Vaccine Production

While protein-glycan coupling technology (PGCT) represents a simplified and cost-effective strategy for bioconjugate vaccine production, it has three main limitations. First, process development timelines, glycosylation pathway design-build-test (DBT) cycles, and bioconjugate production are all limited by cellular growth. Second, it has not yet been shown whether FDA-approved carrier proteins, such as the toxins from *Clostridium tetani* and *Corynebacterium diphtheriae*, have not yet been demonstrated to be compatible with N-linked glycosylation in living *E. coli*. Third, select non-native glycans are known to be transferred with low efficiency by the *C. jejuni* oligosaccharyltransferase (OST), PglB.

A modular, in vitro platform for production of bioconjugates has the potential to address all of these limitations. Here, we demonstrate that bioconjugates against pathogenic strains of *Franciscella tularensis* and *Escherichia coli* can be produced through coordinated in vitro transcription, translation, and N-glycosylation in cell-free glycoprotein synthesis (CFGpS) reactions lasting just 20 hours. This system has the potential to reduce process development and distribution timelines for novel antibacterial vaccines from weeks to days. Further, because of the modular nature of the CFGpS platform and the fact that cell-free systems have demonstrated advantages for production of membrane proteins compared to living cells, this method could be readily applied to produce bioconjugates using FDA-approved carrier proteins, such as the *Clostridium tetani* and *Corynebacterium diphtheriae* toxins, which are membrane localized. This could be accomplished simply by supplying plasmid encoding these carrier proteins to CFGpS reactions. Additionally, because of the modular nature of CFGpS, the in vitro approach could be used to prototype other natural or engineered homologs of the archetypal *C. jejuni* OST to identify candidate OSTs with improved efficiency for transfer of O-antigen LLOs of interest. This can be accomplished by enriching lysates with OSTs of interest and mixing them with LLO lysates in mixed lysate CFGpS reactions, as we have described previously. (See WO 2017/117539, the content of which is incorporated herein by reference in its entirety). Finally, we demonstrate that cell-free bioconjugate synthesis reactions can be lyophilized and retain bioconjugate synthesis capability, demonstrating the potential of the CFGpS system for on-demand, portable, and low cost production or development efforts for novel vaccines. This novel method for in vitro bioconjugate vaccine production has demonstrated advantages for rapid, modular, and portable vaccine prototyping and production compared to existing methods. Our technology enables rapid production of bioconjugate vaccines directed against a user-specified bacterial target for therapeutic development or fundamental research.

The present inventors are not aware of any prokaryotic cell-free system with the capability to produce glycoproteins or bioconjugate vaccines. There are commercial eukaryotic cell lysate systems for cell-free glycoprotein production (Promega, ThermoFisher), but these systems do not involve overexpression of orthogonal glycosylation machinery and do not enable modular, user-specified glycosylation in the way our system can. For this reason, we feel that there is still substantial commercial promise for our invention.

The presently disclosed method for in vitro bioconjugate vaccine production has demonstrated advantages for rapid, modular, and portable vaccine prototyping and production compared to existing methods. This system addresses limitations of existing production approaches, making it an attractive alternative or complementary strategy for antibacterial vaccine production. In light of the growing healthcare concerns caused by antibiotic-resistant bacterial infections, this method has the potential to be extremely valuable for development, production, and distribution of novel vaccines against diverse pathogenic bacterial strains. Advantages of the disclosed method include: on demand expression of bioconjugate vaccines; prototyping novel bioconjugate vaccine candidates; prototyping novel bioconjugate vaccine production pathways; distribution of bioconjugate vaccines to resource-poor settings.

In summary, we disclose the first prokaryotic cell-free system capable of coordinated, cell-free transcription, translation, and glycosylation of glycoprotein vaccines. The disclosed system enables production of bioconjugate vaccines in 20 hours. The modularity of the system enables rapid prototyping of novel glycosylation pathways and vaccine candidates with various carrier proteins. The components and products of the system maybe lyophilized, which enables the potential for broad and rapid distribution of vaccine production technology. The disclosed system reduces the time required to produce bioconjugates in a prokaryotic cell lysate from weeks to days, which could provide competitive advantage in commercialization of the technology.

The disclosed bioconjugates may be formulated as vaccines which optionally may include additional agents for inducing and/or potentiating an immune response such as adjuvants. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants which may be utilized in the disclosed compositions include but are not limited to, co-polymer adjuvants (e.g., Pluronic L121@ brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., AlPO$_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Illustrative Embodiments

The following embodiments are illustrative and are not intended to limit the scope of the claimed subject matter.

Embodiment 1. A method for synthesizing a N-glycosylated recombinant protein carrier which may be utilized as a bioconjugate vaccine, the method comprising performing coordinated transcription, translation, and N-glycosylation of the recombinant protein carrier thereby providing the N-glycosylated recombinant protein carrier which may be utilized as the bioconjugate vaccine, wherein the N-glycosylated recombinant protein carrier comprises: (i) a consensus sequence (which optionally is inserted in the protein carrier), N-X-S/T, wherein X may be any natural or unnatural amino acid except proline; and (ii) at least one antigenic polysaccharide from at least one bacterium N-linked to the recombinant protein carrier, wherein the at least one antigenic polysaccharide optionally is at least one bacterial O-antigen, optionally from one or more strains of *E. coli* or Franciscella *tularensis*; and the bioconjugate vaccine optionally may include an adjuvant.

Embodiment 2. The method of embodiment 1, wherein the carrier protein is an engineered variant of *E. coli* maltose binding protein (MBP).

Embodiment 3. The method of embodiment 1, wherein the carrier protein is a detoxified variant of the toxin from *Clostridium tetani*.

Embodiment 4. The method of embodiment 1, wherein the carrier protein is a detoxified variant of the toxin from *Corynebacterium diphtheriae*.

Embodiment 5. The method of any of the foregoing embodiments, wherein the method utilizes an oligosaccharyltransferase (OST) which is a naturally occurring bacterial homolog of *C. jejuni* PglB.

Embodiment 6. The method of any of embodiments 1-4, wherein the method utilizes an OST that is an engineered variant of *C. jejuni* PglB.

Embodiment 7. The method of any of embodiments 1-4, wherein the method utilizes an OST that is a naturally occurring archaeal OST.

Embodiment 8. The method of any of embodiments 1-4, wherein the method utilizes an OST which is a naturally occurring single-subunit eukaryotic OST, such as those found in *Trypanosoma bruceii*.

Embodiment 9. A method for crude cell lysate preparation in which orthogonal genes or gene clusters are expressed in a source strain for the crude cell lysate, which results in lysates enriched with glycosylation components (lipid-linked oligosaccharides (LLOs), oligosaccharyltransferases (OSTs), and/or both LLOs and OSTs), and optionally which results in a separate lysate enriched with LLOs (e.g., LLOs associated with O-antigen) and a separate lysate enriched with OSTs (e.g., for which the LLOs are a substrate), and optionally combining the separate lysates to perform cell-free protein synthesis of a carrier protein which is glycosylated with the glycan component of the LLOs via the OST's enzyme activity, and further optionally purifying the glycosylated carrier protein and optionally administering the glycosylated carrier protein as an immunogen.

Embodiment 10. The method of embodiment 9, in which the source strain overexpresses a gene encoding an oligosaccharyltransferase (OST).

Embodiment 11. The method of embodiment 9 or 10, in which the source strain overexpresses a synthetic glycosyltransferase pathway, resulting in the production of O-antigens, optionally O-antigens from *F. tularensis* Schu S4 lipid-linked oligosaccharides (FtLLOs).

Embodiment 12. The method of embodiment 9 or 10, in which the source strain overexpresses a synthetic glycosyltransferase pathway, resulting in the production of O-antigens, optionally O-antigens from enterotoxigenic *E. coli* O78 lipid-linked oligosaccharides (EcO78LLOs).

Embodiment 13. The method of any of embodiments 9-12, in which the source strain overexpresses a glycosyltransferase pathway and an OST, resulting in the production of LLOs and OST.

Embodiment 14. The method of embodiment 9 or 10, in which the source strain overexpresses an O-antigen glycosyltransferase pathway from a pathogenic bacterial strain, resulting in the production of O-antigen lipid-linked oligosaccharides (LLOs).

Embodiment 15. A method for cell-free production of a bioconjugate vaccine that involves mixing crude cell lysates (e.g., any of the crude cell lysates of embodiments 9-14).

Embodiment 16. The method of embodiment 15, in which the bioconjugate vaccine comprises an immunogenic carrier that is a protein.

Embodiment 17. The method of embodiment 15, in which the bioconjugate vaccine comprises an immunogenic carrier that is a peptide.

Embodiment 18. The method of any of embodiments 1-17 in which the components of the method may be lyophilized and retain bioconjugate synthesis capability when rehydrated.

Embodiment 19. The method of any of embodiments 15-18 where the goal is on-demand vaccine production.

Embodiment 20. The method of any of embodiments 15-19 where the goal is vaccine production in resource-limited settings.

Embodiment 21. A kit for synthesizing a N-glycosylated carrier protein in vitro, the kit comprising one or more of the following components: (i) a first component comprising a cell lysate that comprises an orthogonal oligosaccharyltransferase (OST); (ii) a second component comprising a cell lysate that comprises an O-antigen (e.g., lipid-linked oligosaccharides (LLOs) comprising O-antigen; (iii) a third component comprising a transcription template and optionally a polymerase for synthesizing an mRNA from the transcription template encoding a carrier protein, the carrier protein comprising an inserted and/or a naturally occurring consensus sequence, N-X-S/T, wherein X may be any natural or unnatural amino acid except proline.

Embodiment 22. The kit of embodiment 21, wherein one or more of the first component, the second component, and the third component are lyophilized and retain biological activity when rehydrated.

Embodiment 23. The kit of embodiment 21 or 22, wherein the first component cell lysate is produced from a source strain (e.g., *E. coli*) that overexpresses a gene encoding the orthogonal OST (e.g. *C. jejuni* PglB).

Embodiment 24. The kit of any of embodiments 21-23, wherein the second component cell lysate is produced from a source strain that overexpresses a synthetic glycosyltransferase pathway (e.g., the biosynthetic machinery to produce the Franciscella *tularensis* Schu S4 O-antigen (FtLLOs lysate) or the biosynthetic machinery to produce the enterotoxigenic *E. coli* O78 lipid-linked oligosaccharides (EcO78LLOs lysate).

Embodiment 25. A method for cell-free production of a glycoprotein which optionally may be a bioconjugate suitable for use as a vaccine, the method comprising: (a) mixing a first cell lysate comprising an orthogonal oligosaccharyltransferase (OST) and a second cell lysate that comprises an O-antigen (e.g., as lipid-linked oligosaccharides (LLOs)) to prepare a cell-free protein synthesis reaction; (b) transcribing and translating a carrier protein in the cell-free protein synthesis reaction (e.g., optionally by adding a transcription template for the carrier protein and/or a polymerase to the cell-free protein synthesis reaction), the carrier protein comprising an inserted and/or naturally occurring consensus sequence, N-X-S/T, wherein X may be any natural or unnatural amino acid except proline; and (c) glycosylating the carrier protein in the cell-free protein synthesis reaction with the bacterial O-antigen.

Embodiment 25. The method of embodiment 24, wherein the second cell lysate comprises the O-antigen as part of lipid-linked oligosaccharides (LLOs).

Embodiment 26. The method of embodiment 24 or 25, further comprising formulating the glycoprotein as a vaccine composition optionally including an adjuvant.

Embodiment 27. A vaccine prepared by any of the foregoing methods and/or kits.

Embodiment 28. A vaccination method comprising administering the vaccine of embodiment 27 to a subject in need thereof.

EXAMPLES

The following Examples are illustrative and are not intended to limit the scope of the claimed subject matter.

Example 1—Method for Rapid In Vitro Synthesis of Bioconjugate Vaccines Via Recombinant Production of N-Glycosylated Proteins in Prokaryotic Cell Lysates Abstract Conjugate vaccines are among the safest and most effective methods for prevention of life-threatening bacterial infections [1-10]. Bioconjugate vaccines are a type of conjugate vaccine produced via protein glycan coupling technology (PGCT), in which polysaccharide antigens are conjugated via N-glycosylation to recombinant carrier proteins using a bacterial oligosaccharyltransferase (OST) in living *Escherichia coli* cells [11]. Bioconjugate vaccines have the potential to greatly reduce the time and cost required to produce antibacterial vaccines. However, PGCT is limited by i) the length of in vivo process development timelines and ii) the fact that FDA-approved carrier proteins, such as the toxins from *Clostridium tetani* and *Corynebacterium diphtheriae*, have not yet been demonstrated to be compatible with N-linked glycosylation in living *E. coli*. Here, we have applied cell-free glycoprotein synthesis (CFGpS) technology to enable rapid in vitro production of bioconjugate vaccines against pathogenic strains of *Escherichia coli* and Franscicella *tularensis* in reactions lasting 20 hours. Due to the modular nature of the CFGpS system, this cell-free strategy could be easily applied to produce bioconjugates using FDA-approved carrier proteins or additional vaccines against pathogenic bacteria whose surface antigen gene clusters are known [11] [9] [7, 10] [3, 5, 6, 8]. We further show that this system can be lyophilized and retain bioconjugate synthesis capability, demonstrating the potential for on-demand vaccine production and development in resource-poor settings. This work represents the first demonstration of bioconjugate vaccine production in *E. coli* lysates and has promising applications as a portable prototyping or production platform for antibacterial vaccine candidates.

Background and Significance

Glycosylation, or the attachment of glycans (sugars) to proteins, is the most abundant post-translational modification in nature and plays a pivotal role in protein folding and activity [1-4]. When it was first discovered in the 1930s [12], glycosylation was thought to be exclusive to eukaryotes. However, glycoproteins were also discovered in archaea in the 1970s [13, 14], and in bacteria in the late 1990s and early 2000s [15, 16], establishing glycosylation as a central post-translational modification in all domains of life. A vast diversity of glycan structures, including both linear and highly branched polysaccharide chains, have been described [17], giving rise to exponentially increased information content compared to other polypeptide modifications [18].

As a consequence of its role in protein structure and information storage, glycosylation is involved in a variety of biological processes. In eukaryotes, glycoproteins are involved in immune recognition and response, intracellular trafficking, and intercellular signaling [19-22]. Furthermore, changes in glycosylation have been shown to correlate with disease states, including cancer [23-25], inflammation [26-29], and Alzheimer's disease [30]. In prokaryotes, glycosylation is known to play important roles in virulence and host invasion [31-33]. Based on the vital role of glycosylation in numerous biological processes, it has been proposed that the central dogma of biology be adapted to include glycans as a central component [34].

The most common forms of glycosylation are asparagine linked (N-linked) and serine (Ser) or threonine (Thr) linked (O-linked) [35]. N-linked glycosylation is characterized by the addition of a glycan moiety to the side chain nitrogen of asparagine (Asn) residues by an oligosaccharyltransferase (OST) that recognizes the consensus sequence Asn-X-Ser/Thr, where X is any amino acid except proline [36, 37]. This process occurs in the endoplasmic reticulum and aids in protein folding, quality control, and trafficking [38]. O-linked glycosylation occurs in the Golgi apparatus following the attachment of N-glycans. Unlike N-linked glycosylation, there is no known consensus sequence for O-linked glycosylation [39, 40]. Despite the importance of glycans in biology, glycoscience was recently identified as an understudied field. A 2012 National Research Council of the U.S. National Academies report highlighted the critical need for transformational advances in glycoscience [41]. The discovery of glycosylation pathways in bacteria is enabling new discoveries about this important post-translational modification [42, 43], but new synthetic and analytical tools are needed to advance the field.

Since the recent discovery of bacterial glycosylation, proteins bearing N- and O-linked glycans have been found in a number of bacteria [44, 45]. The best-studied bacterial glycosylation system is the pgl pathway from *Campylobacter jejuni*, which has been shown to express functionally in *Escherichia coli* (FIG. 1) [46]. In *C. jejuni*, proteins are N-glycosylated with the 1.406 kDa GlcGalNAc$_5$Bac heptasaccharide (Glc: glucose, GalNAc: N-acetylgalactosamine, Bac: bacillosamine). GTs assemble the heptasaccharide onto the lipid anchor undecaprenol pyrophosphate (Und-PP), which is then used as a substrate for the OST (PglB) for N-linked glycosylation [47-49]. This pathway is significantly simpler than eukaryotic glycosylation pathways, and has been leveraged to increase our understanding of the mechanism of N-linked glycosylation [42, 43].

Though not all bacteria synthesize glycoproteins, glycosylation is often involved in the synthesis of the bacterial cell wall. Lipopolysaccharide (LPS) molecules are a major component of the outer membrane of many Gram-negative bacteria, and are made up of a lipid anchor, an oligosaccharide core, and a variable polysaccharide region known as the O-antigen [32]. Capsular polysaccharides (CPS) are another type of surface polysaccharide similar in structure to LPS, except that in this case the polysaccharide region is linked directly to lipid A or a phospholipid anchor [31]. LPS O-antigens (0-PS) and CPS are one of the main tools used by bacterial pathogens for survival in hostile host environments and for host invasion [50-53]. As a result, elucidation of CPS and O-PS biosynthesis mechanisms is of interest for antibiotic and antibacterial vaccine development.

Figure 2:
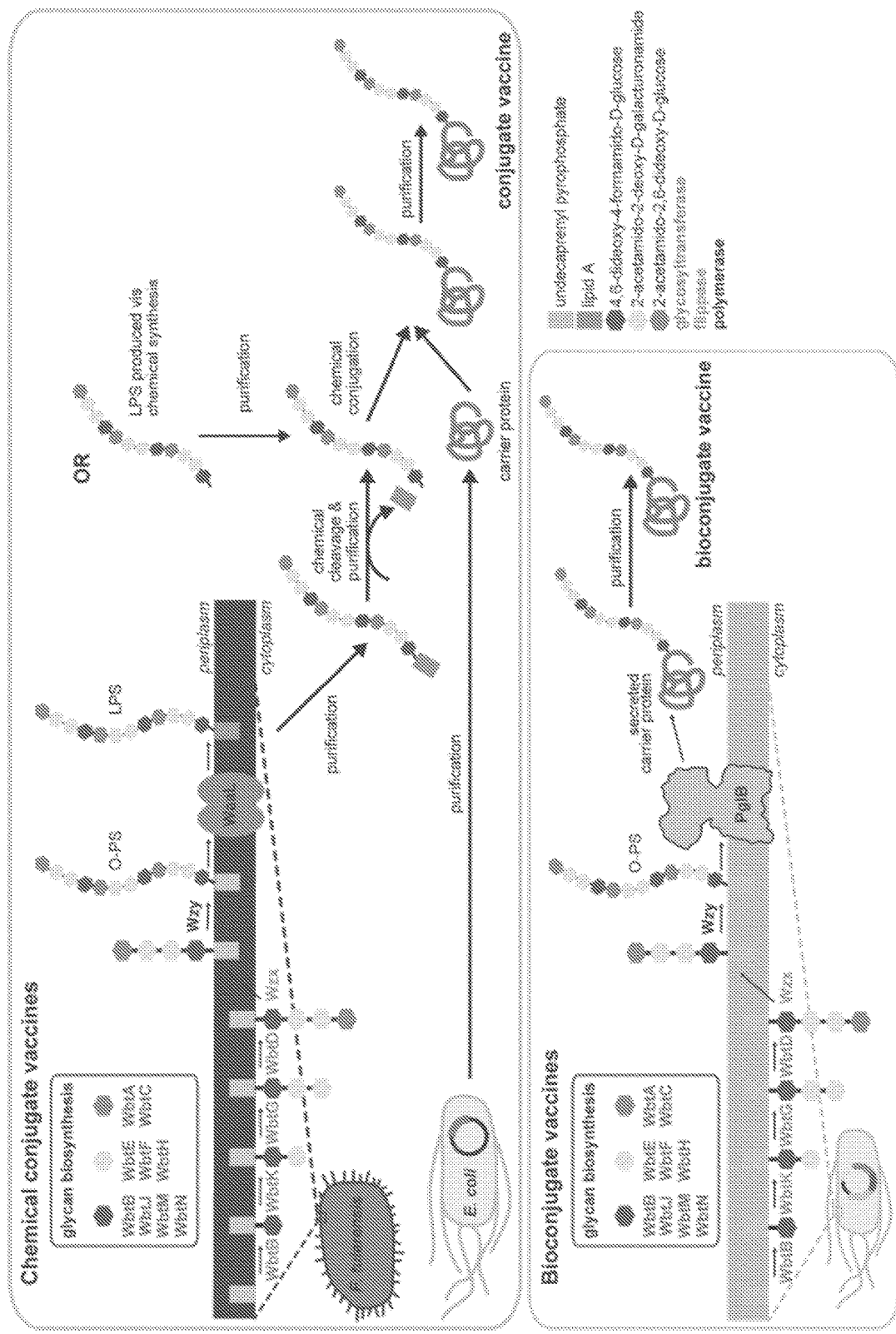
FIG. 2. Strategies for production of conjugate and bioconjugate vaccines as adapted from Ihssen et al., Microb. Cell. Fact. 2010 9:61, pages 1-13, the content of which is incorporated herein by reference in its entirety. The schematic illustrates production of an example vaccine against *Franciscella tularensis*.
Figure 3:
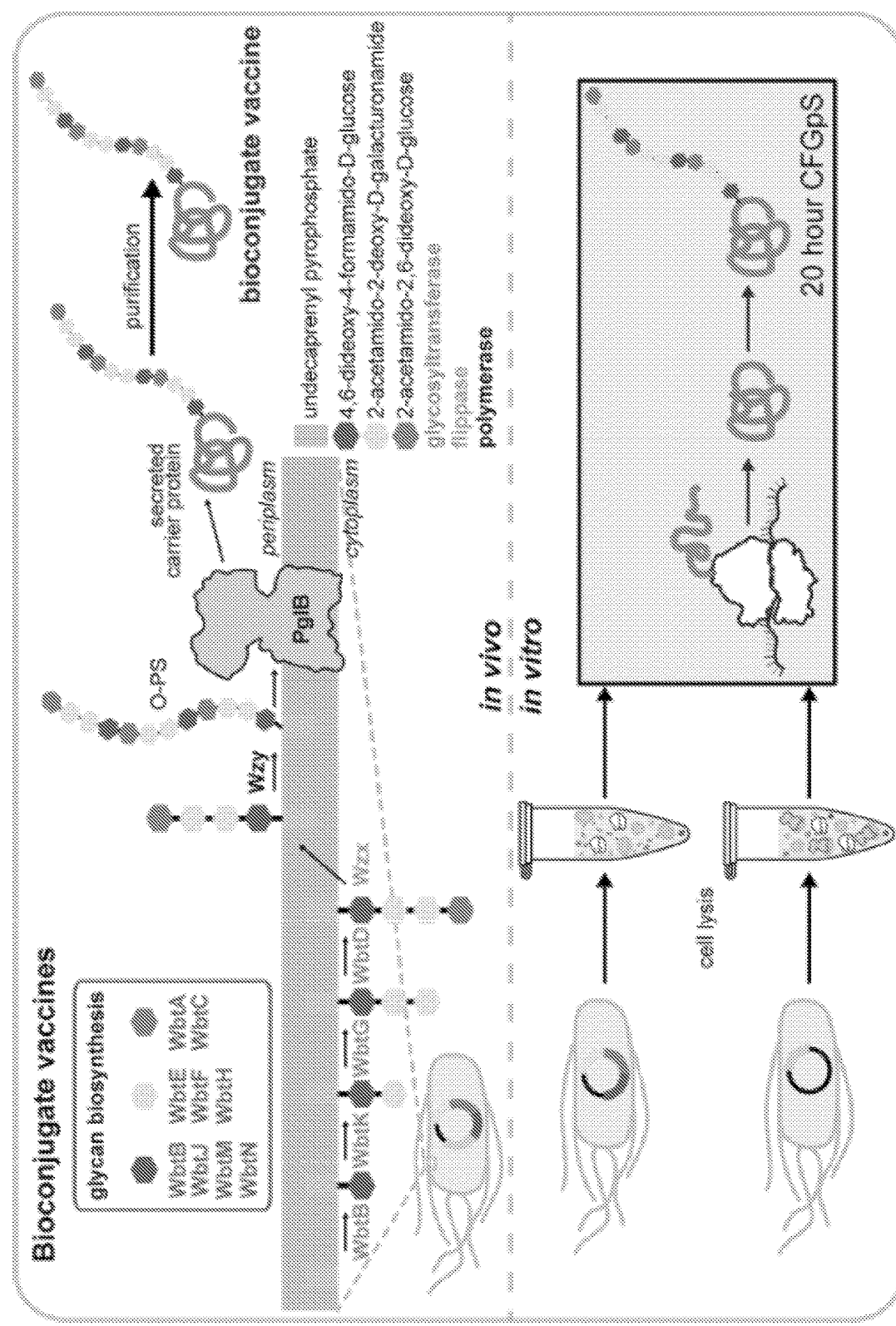
FIG. 3. Application of CFGpS technology for in vitro production of bioconjugate vaccines. Example in vivo and in vitro workflows for production of anti-*F. tularensis* bioconjugates. The ability to produce bioconjugates in vitro will enable rapid prototyping of novel vaccine candidates.
Figure 4:
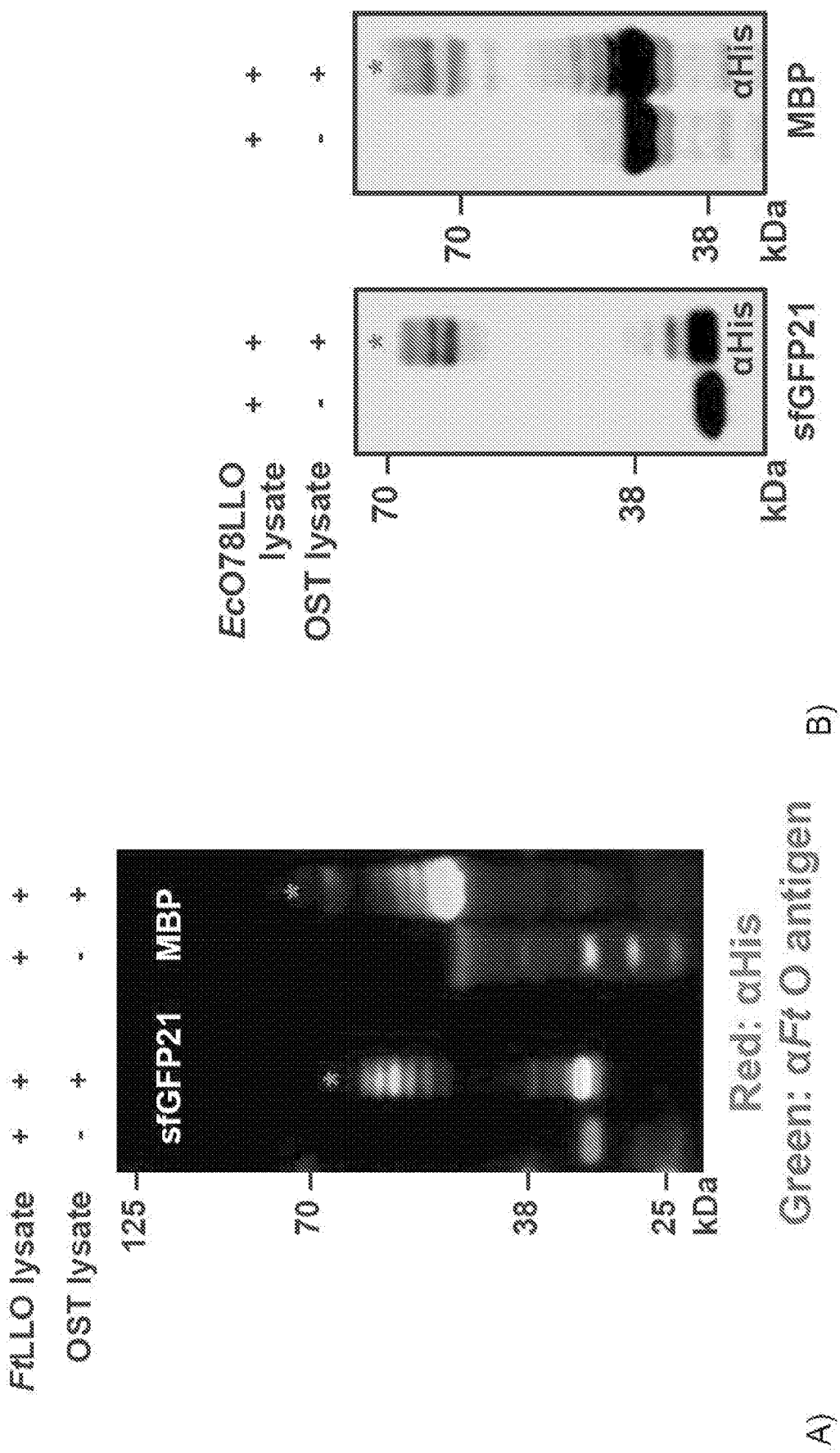
FIG. 4. Rapid synthesis of glycoproteins bearing diverse bacterial 0-antigens in mixed lysate CFGpS. S30 lysates were prepared from CLM24 cells expressing the *C. jejuni* OST (CjOST lysate), the Franciscella *tularensis* O-antigen (FtO-PS) biosynthesis pathway (FtLLO lysate), or the *Escherichia coli* O78 antigen (EcO78-PS) biosynthesis pathway (EcO78LLO lysate). (A) FtLLO lysate was mixed with CjOST lysate in CFGpS reactions containing DNA template for either sfGFP21-DQNAT-6×His or MBP-4×DQNAT-6×His. The FtO-PS is covalently attached to R4-DQNAT and MBP-4×DQNAT when both the CcOST and FtLLO lysate are present in the CFGpS reaction, indicated by the ladder-like pattern observed in the Western blot assay (lanes 2, 4). (B) EcO78LLO lysate was mixed with CjOST lysate in CFGpS reactions containing DNA template for either sfGFP21-DQNAT-6×His, or MBP-4×DQNAT-6×
Figure 5:
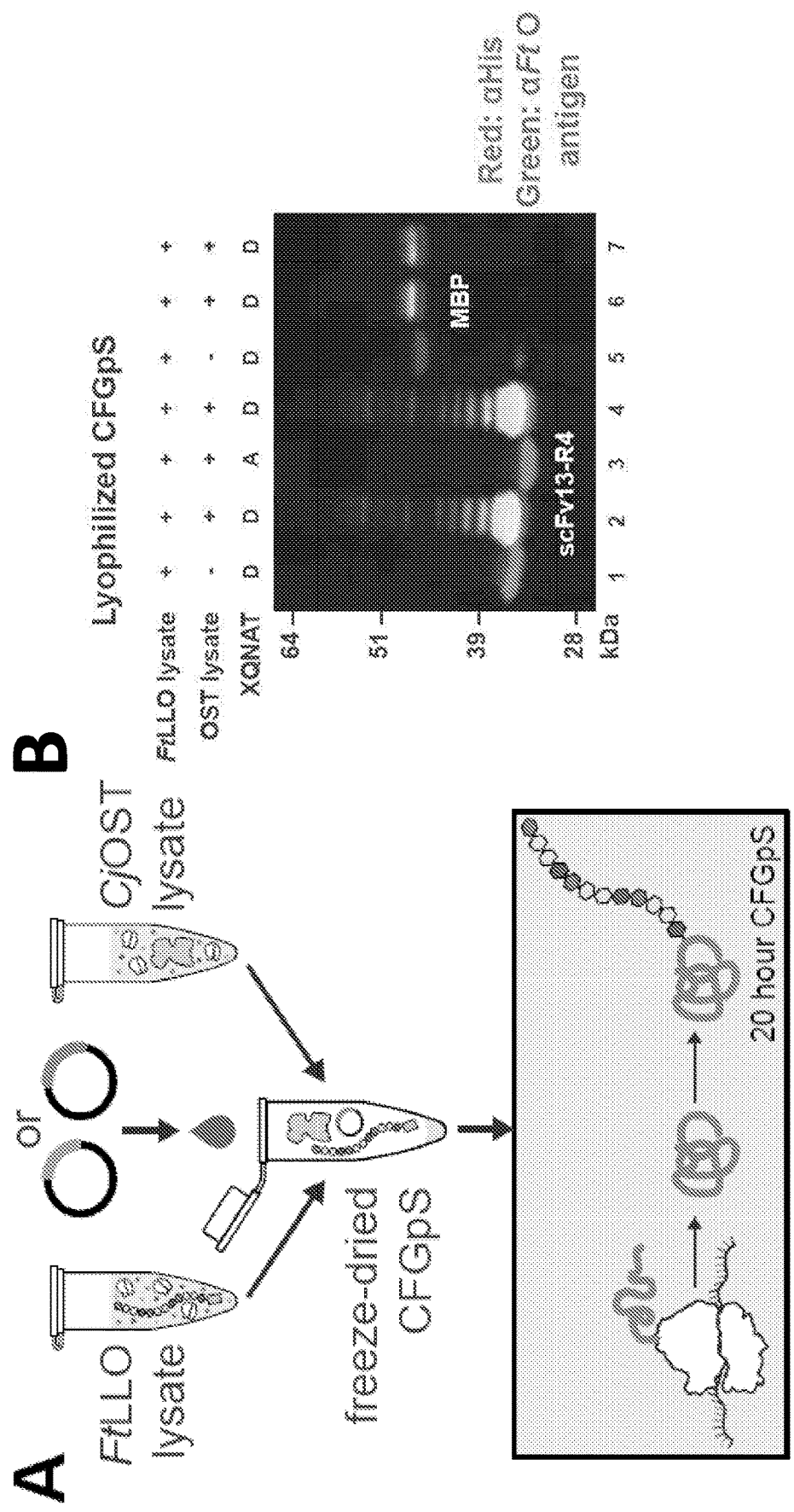
Figure 6:
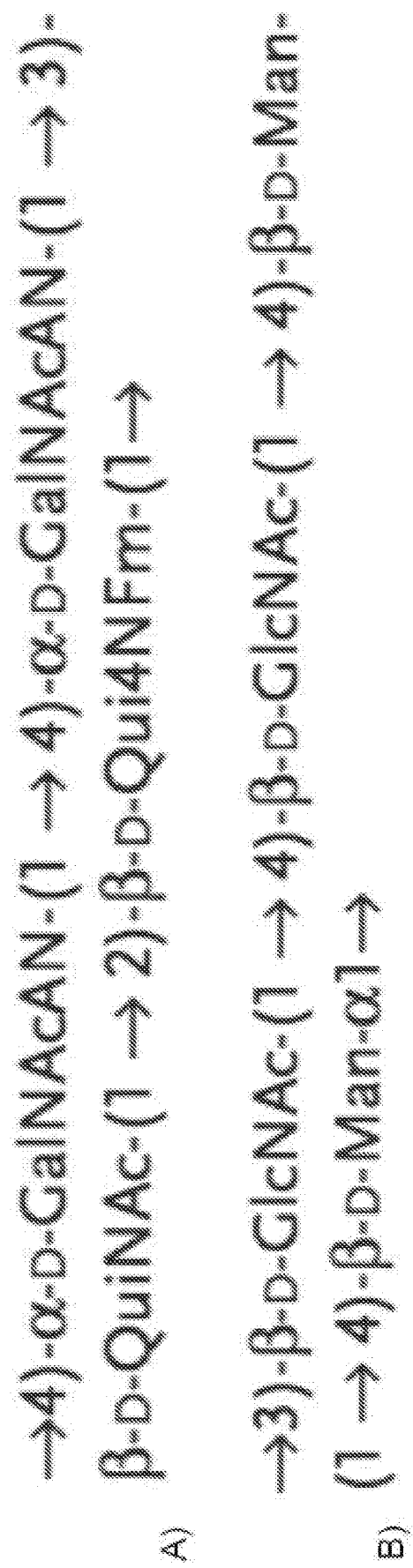

The rise of antibiotic-resistant bacterial strains necessitates the development of novel strategies for treatment and prevention of life-threatening bacterial infections. In 2013, the Center for Disease Control and Prevention released a report citing antibiotic resistance as one of United States' most serious health threats. Conjugate vaccines, which consist of CPS or O-PS antigens covalently linked to carrier proteins, are among the safest and most effective preventative measures against bacterial infections and have been used to reduce the incidence of *Streptococcus pneumoniae*, *Neisseria meningitides*, and *Haemophilus* influenza infection [1-10]. Because polysaccharide antigens cannot directly activate naïve T cells, they must be conjugated to a carrier protein in order to induce long-lasting immunological memory [54]. However, existing technologies for producing conjugate vaccines are complex, involve multiple processing and purification steps, and the resulting products are ill-defined (FIG. 2, top) [2]. Additionally, these processes are time-consuming and can require large-scale fermentation of pathogenic bacteria, making conjugate vaccines prohibitively expensive for vaccination campaigns in developing nations.

The production of recombinant O antigen-protein conjugates in living *E. coli* cells was recently accomplished using bacterial N-glycosylation machinery (FIG. 2, bottom) [11]. These so-called bioconjugate vaccines have the potential to reduce the cost and time required for antibacterial vaccine production. Bioconjugates have been developed against several bacterial targets, including Franciscella *tularensis* [4], *Pseudomonas aeruginosa* [11], *Salmonella enterica* [9], *Shigella* dynsenteriae [7, 10], *Shigella flexneri* [8], *Staphylococcus aureus* [5], *Brucella abortus* [3], and *Burkholderia pseudomallei* [6]. An in vitro method for bioconjugate production could shorten process development timelines for novel antibacterial vaccines from months to weeks [55].

Cell-free protein synthesis (CFPS) is an emerging field that allows for the production of proteins in crude cell lysates [55, 56]. CFPS technology was first used over 50 years ago by Nirenberg and Matthaei to decipher the genetic code [57]. In the late 1960s and early 1970s, CFPS was employed to help elucidate the regulatory mechanisms of the *E. coli* lactose [58] and tryptophan [59] operons. In the last two decades, CFPS platforms have experienced a surge in development to meet the increasing demand for recombinant protein expression technologies [55].

CFPS offers several advantages for recombinant protein expression. In particular, the open reaction environment allows for addition or removal of substrates for protein synthesis, as well as precise, on-line reaction monitoring. Additionally, the CFPS reaction environment can be wholly directed toward and optimized for production of the protein product of interest. CFPS effectively decouples the cell's objectives (growth & reproduction) from the engineer's objectives (protein overexpression & simple product purification), which has proven advantageous for the production of complex proteins and protein assemblies, including membrane proteins [60-63], bispecific antibodies [64], antibody-drug conjugates [65], and virus-like particle vaccines [66-68]. Overall, CFPS technology allows for shortened protein synthesis timelines and increased flexibility for addition or removal of substrates compared to in vivo approaches. The *E. coli* CFPS system in particular has been widely adopted because of i) its high batch yields, with up to 2.3 g/L of green fluorescent protein (GFP) reported [69], ii) inexpensive required substrates [70-72], and iii) the ability to linearly scale reaction volumes over 106 L [73].

Glycosylation is possible in some eukaryotic CFPS systems, including ICE, CHO extract, and a human leukemia cell line extract [74-77]. However, these platforms harness the endogenous machinery to carry out glycosylation meaning that i) the possible glycan structures are restricted to those naturally synthesized by the host cells and ii) the glycosylation process is carried out in a "black box" and thus difficult to engineer or control. The development of a highly active *E. coli* CFPS platform has prompted recent efforts to enable glycoprotein production in *E. coli* lysates through the addition of orthogonal glycosylation components. In one study, Guarino and DeLisa demonstrated the ability to produce glycoproteins in *E. coli* CFPS by adding purified lipid-linked oligosaccharides (LLOs) and the C. Jejuni OST to a CFPS reaction. Yields of between 50-100 µg/mL of AcrA, a *C. jejuni* glycoprotein, were achieved [78]. Despite these recent advances, bacterial cell-free glycosylation systems have been limited by their inability to co-activate efficient protein synthesis and glycosylation. We recently developed a cell-free glycoprotein synthesis (CFGpS) system that addresses this limitation by enabling modular, coordinated transcription, translation, and N-glycosylation of proteins in *E. coli* lysates selectively enriched with glycosylation enzymes (see WO 2017/117539, the content of which is incorporated herein by reference in its entirety). Here, we apply this technology platform to the production of bioconjugate vaccines to yield a methodology for rapid, modular in vitro expression of bioconjugates.

Results and Discussion

Cell-free Glycoprotein Synthesis (CFGpS) for Bioconjugate Vaccine Production. While protein-glycan coupling technology (PGCT) represents a simplified and cost-effective strategy for bioconjugate vaccine production, it has three main limitations. First, process development timelines, glycosylation pathway design-build-test (DBT) cycles, and bioconjugate production are all limited by cellular growth. Second, it has not yet been shown whether FDA-approved carrier proteins, such as the toxins from *Clostridium tetani* and *Corynebacterium diphtheriae*, have not yet been demonstrated to be compatible with N-linked glycosylation in living *E. coli*. Third, select non-native glycans are known to be transferred with low efficiency by the *C. jejuni* OST, PglB [9].

A modular, in vitro platform for production of bioconjugates has the potential to address all of these limitations. Here, we demonstrate that bioconjugates against pathogenic strains of *Franciscella tualrensis* and *Escherichia coli* can be produced through coordinated in vitro transcription, translation, and N-glycosylation in cell-free glycoprotein synthesis (CFGpS) reactions lasting just 20 hours. This system has the potential to reduce process development and distribution timelines for novel antibacterial vaccines from weeks to days. Further, because of the modular nature of the CFGpS platform and the fact that cell-free systems have demonstrated advantages for production of membrane proteins compared to living cells [60-63], this method could be readily applied to produce bioconjugates using FDA-approved carrier proteins, such as the *Clostridium tetani* and *Corynebacterium diphtheriae* toxins, which are membrane localized. This could be accomplished simply by supplying plasmid encoding these carrier proteins to CFGpS reactions. Additionally, because of the modular nature of CFGpS, the in vitro approach could be used to prototype other natural or engineered homologs of the archetypal *C. jejuni* OST, such as those described recently [9, 79, 80], to identify candidate OSTs with improved efficiency for transfer of O-antigen LLOs of interest. This can be accomplished by enriching lysates with OSTs of interest and mixing them with LLO lysates in mixed lysate CFGpS reactions, as we have described previously (Jewett lab, unpublished data; U.S. Provisional Patent Application 62/273,124). Finally, we demonstrate that cell-free bioconjugate synthesis reactions can be lyophilized and retain bioconjugate synthesis capability, demonstrating the potential of the CFGpS system for on-demand, portable, and low cost production or development efforts for novel vaccines. This novel method for in vitro bioconjugate vaccine production has demonstrated advantages for rapid, modular, and portable vaccine prototyping and production compared to existing methods.

Bioconjugate vaccines against *F. tularensis* can be synthesized in vitro via CFGpS. Francisella *tularensis* is a gram-negative bacterium that causes tularemia. *F. tularensis* is considered one of the most infectious bacteria known to man: a single inhaled *bacillus* results in infection of 40-50% of individuals, with a mortality rate of up to 30% [81]. The gene locus for O-antigen biosynthesis was recently characterized [82] and used to create a bioconjugate vaccine in living *E. coli* cells [4]. We decided to use this pathway to produce an anti-*F. tularensis* bioconjugate vaccine using CFGpS. We hypothesized that anti-*F. tularensis* bioconjugate vaccines can be synthesized in vitro using CFGpS technology (FIG. 3).

We hypothesized that Und-PP-linked polysaccharide antigens can be enriched in S30 lysates via overexpression of orthogonal glycosylation machinery in an *E. coli* CFGpS chassis strain lacking the WaaL O-antigen ligase. To test this hypothesis, we produced lysates from CLM24 cells overexpressing the *C. jejuni* OST, PglB (CjOST lysate) and the biosynthetic machinery to produce the Francisella *tularensis* Schu S4 O antigen (FtLLO lysate). This 17 kb gene cluster from *F. tularensis* Schu S4 contains 15 predicted open reading frames (ORFs) and produces oligosaccharides comprised of the repeating unit $GalNAcAN_2QuiNAcQui4NFm$ (GalNAcAN: 2-acetamido-2-deoxy-D-galacturonamide, QuiNAc: 2-acetamido-2,6-dideoxy-D-glucose, Qui4NFm: 4,6-dideoxy-4-formamido-D-glucose) (FIG. 6A) [82]. Lysates were prepared via high-pressure homogenization, to encourage formation of soluble inverted membrane vesicles, which carry membrane-bound components, such as FtLLOs and CjOST, into the crude lysate.

We hypothesized that anti-*F. tularensis* bioconjugate vaccines can be synthesized in vitro using CFGpS technology. To produce bioconjugates bearing the *F. tularensis* O polysaccharide (FtO-PS), CjPglB lysate was mixed with FtLLO lysate in CFGpS reactions lasting 20 hours at 30° C. These reactions contained plasmid encoding either i) super-folder green fluorescent protein engineered to include a DQNAT sequon in a flexible linker inserted at residue T216 and a C-terminal His tag (sfGFP-21-DQNAT-6×His) or ii) an engineered maltose binding protein construct with four C-terminal repeats of the DQNAT sequon and a C-terminal His tag (MBP-4×DQNAT-6×His). Bioconjugates composed of *E. coli* O-antigens conjugated to MBP-4×DQNAT-6×His were recently shown to elicit humoral and cellular immunity in mice [83]. Within the first hour of the CFGpS reaction, reaction mixtures were spiked with manganese chloride ($MnCl_2$) and n-dodecyl-β-D-maltopyranoside (DDM) detergent at final concentrations of 25 mM $MnCl_2$, 0.1% w/v DDM to optimize CjPglB activity (Jewett lab, unpublished data). After the CFGpS reactions were allowed to proceed for a total of 20 hours at 30° C., glycosylation activity was assayed via immunoblotting with anti-His antibody and a commercial monoclonal antibody specific to FtO-PS. The ladder-like pattern observed when the FtLLO and CjPglB lysates are mixed is indicative of FtLLO attachment and results from O-PS chain length variability through the action of the Wzy polymerase (FIG. 4A) [4, 11]. These results demonstrate the integration of coordinated cell-free carrier protein synthesis and O-antigen attachment for the first time. Furthermore, we show that cell-free bioconjugate synthesis occurs in just 20 hours, making this cell-free platform an attractive option for rapid production and prototyping of bioconjugate vaccine candidates.

Bioconjugate vaccines against *E. coli* O78 and other pathogenic strains can be readily synthesized due to the modular nature of CFGpS platform. To demonstrate the generality and modularity of the CFGpS approach for bioconjugate production, we sought to produce bioconjugates against an additional pathogenic bacterium. We decided to synthesize bioconjugates against enterotoxigenic *E. coli* strain O78, since its biosynthetic pathway has been described previously [84] and there exists a commercial antiserum specific to this strain. The *E. coli* O78 gene cluster was cloned and is encoded in plasmid pMW07-O78. Expression of the *E. coli* O78 gene cluster results in production of an O-antigen with the repeating unit $GlcNAc_2Man_2$ (GlcNAC: N-acetylglucosamine; Man: mannose) (FIG. 6B)

We prepared lysates enriched with *E. coli* O78 antigen LLOs (EcO78LLO lysate) from CLM24 cells expressing pMW07-O78 using the same method described above. We then mixed the EcO78LLO lysate with CjOST lysate in CFGpS reactions containing plasmid encoding either sfGFP21-DQNAT-6×His or MBP-4×DQNAT-6×His. CFGpS reactions were run as described above. Glycosylation activity was assayed via immunoblotting with an anti-His antibody and a commercial antiserum against the *E. coli* O78 strain. Again, a ladder-like pattern is observed when both EcO78LLO lysate and CjOST lysates are present in the reaction, indicating successful conjugation of the EcO78-PS (FIG. 4B). The bioconjugates were also cross-reactive with the anti-EcO78 serum (data not shown). These results demonstrate the modular nature of the in vitro approach, and provide evidence that the CFGpS platform could be used to produce bioconjugate vaccines targeting many different pathogenic bacterial strains. Attractive candidates include pathogenic bacteria whose surface antigen gene clusters are known, including *Pseudomonas aeruginosa* [11], *Salmonella enterica* [9], *Shigella* dynsenteriae [7, 10], *Shigella flexneri* [8], *Staphylococcus aureus* [5], *Brucella abortus* [3], and *Burkholderia pseudomallei* [6]. These results demonstrate the potential of the in vitro system for rapid production or prototyping of vaccine candidates directed against diverse pathogenic bacteria. Moreover, because synthesis can be achieved in just 20 h with different O-PS antigens, this cell-free platform represents an attractive option for rapid production and prototyping of novel bioconjugate vaccine candidates.

Lyophilized CFGpS reactions retain bioconjugate synthesis capability. A major limitation of traditional conjugate vaccines is their high cost, due to their time consuming production process. By comparison, bioconjugate vaccines are less expensive to produce, however, production time is dictated by the time required to ferment and purify proteins from living cells. We wanted to test whether our CFGpS reactions could be freeze-dried for potential room-temperature storage and distribution to enable faster production and broader-reaching vaccination campaigns and development efforts compared to in vivo approaches. To test whether this was possible, CFGpS reactions were prepared containing either CjOST lysate or FtLLO lysate alone, or a mixture of both CjOST and FtLLO lysates. These reactions were then lyophilized and reconstituted with L nuclease-free water. The reactions contained plasmid encoding either a short chain antibody fragment with a C-terminal DQNAT sequon followed by a His tag (scFv13-R4-DQNAT-6×His) or MBP-4×DQNAT-6×His. Pre-mixed reactions (lanes 1, 2, 5, 6) were run directly following reconstitution, while reactions containing CjOST lysate or FtLLO lysate alone were mixed following reconstitution (lanes 3, 4, 7). The FtO-PS is attached to the target protein when the DQNAT sequon is synthesized and both CjOST lysate or FtLLO lysate are present in the reaction (lanes 2, 4, 6, 7). These results confirm that the CFGpS reaction mixture can be lyophilized without loss of bioconjugate synthesis capability, highlighting the potential of our technology for portable, on-demand vaccine production and long-term, refrigeration-free storage.

CONCLUSIONS

We describe here a novel method for coordinated in vitro transcription, translation, and conjugation of vaccine antigens to carrier proteins. This in vitro approach uniquely (i) decouples cell viability from glycosylation activity and enables reduction of cellular metabolic burden through in vitro reconstitution of glycosylation components, (ii) permits design-build-test (DBT) iterations on individual glycosylation components, and (iii) allows for assembly of glycosylation pathways within well-defined experimental conditions including chemical and physical manipulations not possible in cells. Further, the system has obvious and commercially attractive applications to producing bioconjugates using FDA-approved carrier proteins, such as the toxins from *Clostridium tetani* and *Corynebacterium diphtheriae*. This novel method for in vitro bioconjugate vaccine production has demonstrated advantages for rapid, modular, and portable vaccine prototyping and production compared to existing methods.

REFERENCES

1. Maue, A. C., F. Poly, and P. Guerry, A capsule conjugate vaccine approach to prevent diarrheal disease caused by *Campylobacter jejuni*. Hum Vaccin Immunother, 2014. 10(6): p. 1499-504.
2. Anderson, P., Antibody responses to *Haemophilus influenzae* type b and diphtheria toxin induced by conjugates of oligosaccharides of the type b capsule with the non-toxic protein CRM197. Infect Immun, 1983. 39(1): p. 233-8.
3. Iwashkiw, J. A., et al., Exploiting the *Campylobacter jejuni* protein glycosylation system for glycoengineering vaccines and diagnostic tools directed against brucellosis. Microb Cell Fact, 2012. 11: p. 13.
4. Cuccui, J., et al., Exploitation of bacterial N-linked glycosylation to develop a novel recombinant glycoconjugate vaccine against *Francisella tularensis*. Open Biol, 2013. 3(5): p. 130002.
5. Wacker, M., et al., Prevention of *Staphylococcus aureus* infections by glycoprotein vaccines synthesized in *Escherichia coli*. J Infect Dis, 2014. 209(10): p. 1551-61.
6. Garcia-Quintanilla, F., et al., Production of a recombinant vaccine candidate against *Burkholderia pseudomallei* exploiting the bacterial N-glycosylation machinery. Front Microbiol, 2014. 5: p. 381.
7. Ravenscroft, N., et al., Purification and characterization of a *Shigella* conjugate vaccine, produced by glycoengineering *Escherichia coli*. Glycobiology, 2015.
8. Kampf, M. M., et al., In vivo production of a novel glycoconjugate vaccine against *Shigella flexneri* 2a in recombinant *Escherichia coli*: identification of stimulating factors for in vivo glycosylation. Microb Cell Fact, 2015. 14: p. 12.
9. Ihssen, J., et al., Increased efficiency of *Campylobacter jejuni* N-oligosaccharyltransferase PglB by structure-guided engineering. Open Biol, 2015. 5(4).
10. Ihssen, J., et al., Production of glycoprotein vaccines in *Escherichia coli*. Microb Cell Fact, 2010. 9: p. 61.
11. Feldman, M. F., et al., Engineering N-linked protein glycosylation with diverse O antigen lipopolysaccharide structures in *Escherichia coli*. Proc Natl Acad Sci USA, 2005. 102(8): p. 3016-21.
12. Neuberger, A., Carbohydrates in protein: The carbohydrate component of crystalline egg albumin. Biochem J, 1938. 32(9): p. 1435-51.
13. Mescher, M. F. and J. L. Strominger, Purification and characterization of a prokaryotic glucoprotein from the cell envelope of *Halobacterium* salinarium. J Biol Chem, 1976. 251(7): p. 2005-14.
14. Sleytr, U. B., Heterologous reattachment of regular arrays of glycoproteins on bacterial surfaces. Nature, 1975. 257(5525): p. 400-2.
15. Szymanski, C. M., et al., Evidence for a system of general protein glycosylation in *Campylobacter jejuni*. Mol Microbiol, 1999. 32(5): p. 1022-30.
16. Linton, D., et al., Identification of N-acetylgalactosamine-containing glycoproteins PEB3 and CgpA in *Campylobacter jejuni*. Mol Microbiol, 2002. 43(2): p. 497-508.
17. Spiro, R. G., Protein glycosylation: nature, distribution, enzymatic formation, and disease implications of glycopeptide bonds. Glycobiology, 2002. 12(4): p. 43R-56R.
18. Laine, R. A., The Information-Storing Potential of the Sugar Code. Glycosciences: Status and Perspectives, 1997: p. 1-14.
19. Raman, R., et al., Glycomics: an integrated systems approach to structure-function relationships of glycans. Nat Methods, 2005. 2(11): p. 817-24.
20. Ohtsubo, K. and J. D. Marth, Glycosylation in cellular mechanisms of health and disease. Cell, 2006. 126(5): p. 855-67.
21. Imberty, A. and A. Varrot, Microbial recognition of human cell surface glycoconjugates. Curr Opin Struct Biol, 2008. 18(5): p. 567-76.
22. Daniels, M. A., K. A. Hogquist, and S. C. Jameson, Sweet 'n' sour: the impact of differential glycosylation on T cell responses. Nat Immunol, 2002. 3(10): p. 903-10.

23. Dube, D. H. and A. R. Bertozzi, Glycans in cancer and inflammation—potential for therapeutics and diagnostics. Nat Rev Drug Discov, 2005. 4: p. 477-88.
24. Pinho, S. S. and C. A. Reis, Glycosylation in cancer: mechanisms and clinical implications. Nat Rev Cancer, 2015. 15(9): p. 540-55.
25. Ma, Z. and K. Vosseller, Cancer metabolism and elevated 0-GlcNAc in oncogenic signaling. J Biol Chem, 2014. 289(50): p. 34457-65.
26. Theodoratou, E., et al., The role of glycosylation in IBD. Nat Rev Gastroenterol Hepatol, 2014. 11(10): p. 588-600.
27. Albrecht, S., et al., Glycosylation as a marker for inflammatory arthritis. Cancer Biomark, 2014. 14(1): p. 17-28.
28. Axford, J. S., Glycosylation and rheumatic disease. Biochim Biophys Acta, 1999. 1455(2-3): p. 219-29.
29. Baudoin, L. and T. Issad, 0-GlcNAcylation and Inflammation: A Vast Territory to Explore. Front Endocrinol (Lausanne), 2014. 5: p. 235.
30. Wang, J. Z., I. Grundke-Iqbal, and K. Iqbal, Glycosylation of microtubule-associated protein tau: an abnormal posttranslational modification in Alzheimer's disease. Nat Med, 1996. 2(8): p. 871-5.
31. Guerry, P., et al., *Campylobacter* polysaccharide capsules: virulence and vaccines. Front Cell Infect Microbiol, 2012. 2: p. 7.
32. Kalynych, S., R. Morona, and M. Cygler, Progress in understanding the assembly process of bacterial O-antigen. FEMS Microbiol Rev, 2014. 38(5): p. 1048-65.
33. Bacon, D. J., et al., A phase-variable capsule is involved in virulence of *Campylobacter jejuni* 81-176. Mol Microbiol, 2001. 40(3): p. 769-77.
34. Wang, L. X. and B. G. Davis, Realizing the Promise of Chemical Glycobiology. Chem Sci, 2013. 4(9): p. 3381-3394.
35. Chauhan, J. S., A. Rao, and G. P. Raghava, In silico platform for prediction of N-, O- and C-glycosites in eukaryotic protein sequences. PLoS One, 2013. 8(6): p. e67008.
36. Gavel, Y. and G. von Heijne, Sequence differences between glycosylated and non-glycosylated Asn-X-Thr/Ser acceptor sites: implications for protein engineering. Protein Eng, 1990. 3(5): p. 433-42.
37. Lehle, L. and W. Tanner, Glycosyl transfer from dolichyl phosphate sugars to endogenous and exogenous glycoprotein acceptors in yeast. Eur J Biochem, 1978. 83(2): p. 563-70.
38. Varki, A., Biological roles of oligosaccharides: all of the theories are correct. Glycobiology, 1993. 3(2): p. 97-130.
39. Wilson, I. B., Y. Gavel, and G. von Heijne, Amino acid distributions around O-linked glycosylation sites. Biochem J, 1991. 275 (Pt 2): p. 529-34.
40. Thanka Christlet, T. H. and K. Veluraja, Database analysis of O-glycosylation sites in proteins. Biophys J, 2001. 80(2): p. 952-60.
41. Walt, D., et al., Transforming Glycoscience: A Roadmap for the Future. 2012: The National Academies Press.
42. Lizak, C., et al., X-ray structure of a bacterial oligosaccharyltransferase. Nature, 2011. 474(7351): p. 350-355.
43. Perez, C., et al., Structure and mechanism of an active lipid-linked oligosaccharide flippase. Nature, 2015. 524 (7566): p. 433-8.
44. Abu-Qarn, M., J. Eichler, and N. Sharon, Not just for Eukarya anymore: protein glycosylation in Bacteria and Archaea. Curr Opin Struct Biol, 2008. 18(5): p. 544-50.
45. Weerapana, E. and B. Imperiali, Asparagine-linked protein glycosylation: from eukaryotic to prokaryotic systems. Glycobiology, 2006. 16(6): p. 91R-101R.
46. Wacker, M., et al., N-linked glycosylation in *Campylobacter jejuni* and its functional transfer into *E. coli*. Science, 2002. 298(5599): p. 1790-3.
47. Glover, K. J., et al., Direct biochemical evidence for the utilization of UDP-bacillosamine by PglC, an essential glycosyl-1-phosphate transferase in the *Campylobacter jejuni* N-linked glycosylation pathway. Biochemistry, 2006. 45(16): p. 5343-50.
48. Glover, K. J., E. Weerapana, and B. Imperiali, In vitro assembly of the undecaprenylpyrophosphate-linked heptasaccharide for prokaryotic N-linked glycosylation. Proc Natl Acad Sci USA, 2005. 102(40): p. 14255-9.
49. Olivier, N. B., et al., In vitro biosynthesis of UDP-N, N'-diacetylbacillosamine by enzymes of the *Campylobacter jejuni* general protein glycosylation system. Biochemistry, 2006. 45(45): p. 13659-69.
50. Murray, G. L., S. R. Attridge, and R. Morona, Regulation of *Salmonella typhimurium* lipopolysaccharide O antigen chain length is required for virulence; identification of FepE as a second Wzz. Mol Microbiol, 2003. 47(5): p. 1395-406.
51. Murray, G. L., S. R. Attridge, and R. Morona, Altering the length of the lipopolysaccharide O antigen has an impact on the interaction of *Salmonella enterica* serovar *Typhimurium* with macrophages and complement. J Bacteriol, 2006. 188(7): p. 2735-9.
52. Duerr, C. U., et al., O-antigen delays lipopolysaccharide recognition and impairs antibacterial host defense in murine intestinal epithelial cells. PLoS Pathog, 2009. 5(9): p. e1000567.
53. Saldias, M. S., X. Ortega, and M. A. Valvano, *Burkholderia cenocepacia* O antigen lipopolysaccharide prevents phagocytosis by macrophages and adhesion to epithelial cells. J Med Microbiol, 2009. 58(Pt 12): p. 1542-8.
54. Lesinski, G. B. and M. A. Westerink, Novel vaccine strategies to T-independent antigens. J Microbiol Methods, 2001. 47(2): p. 135-49.
55. Carlson, E. D., et al., Cell-free protein synthesis: applications come of age. Biotechnol Adv, 2012. 30(5): p. 1185-94.
56. Hodgman, C. E. and M. C. Jewett, Cell-free synthetic biology: thinking outside the cell. Metab Eng, 2012. 14(3): p. 261-9.
57. Nirenberg, M. W. and J. H. Matthaei, The dependence of cell-free protein synthesis in *E. coli* upon naturally occurring or synthetic polyribonucleotides. Proc Natl Acad Sci USA, 1961. 47: p. 1588-602.
58. Chambers, D. A. and G. Zubay, The stimulatory effect of cyclic adenosine 3'5'-monophosphate on DNA-directed synthesis of beta-galactosidase in a cell-free system. Proc Natl Acad Sci USA, 1969. 63(1): p. 118-22.
59. Zalkin, H., C. Yanofsky, and C. L. Squires, Regulated in vitro synthesis of *Escherichia coli* tryptophan operon messenger ribonucleic acid and enzymes. J Biol Chem, 1974. 249(2): p. 465-75.
60. Matthies, D., et al., Cell-free expression and assembly of ATP synthase. J Mol Biol, 2011. 413(3): p. 593-603.
61. Kaiser, L., et al., Efficient cell-free production of olfactory receptors: detergent optimization, structure, and ligand binding analyses. Proc Natl Acad Sci USA, 2008. 105(41): p. 15726-31.
62. Wang, X., et al., Peptide surfactants for cell-free production of functional G protein-coupled receptors. Proc Natl Acad Sci USA, 2011. 108(22): p. 9049-54.

63. Bernhard, F. and Y. Tozawa, Cell-free expression—making a mark. Curr Opin Struct Biol, 2013. 23(3): p. 374-80.
64. Xu, Y., et al. Production of bispecific antibodies in "Knobs-into-Holes" using a cell-free expression system. in mAbs. 2014. Taylor & Francis.
65. Zimmerman, E. S., et al., Production of Site-Specific Antibody-Drug Conjugates Using Optimized Non-Natural Amino Acids in a Cell-Free Expression System. Bioconjugate Chemistry, 2014. 25(2): p. 351-361.
66. Ng, P. P., et al., A vaccine directed to B cells and produced by cell-free protein synthesis generates potent antilymphoma immunity. Proc Natl Acad Sci USA, 2012. 109(36): p. 14526-31.
67. Lu, Y., J. P. Welsh, and J. R. Swartz, Production and stabilization of the trimeric influenza hemagglutinin stem domain for potentially broadly protective influenza vaccines. Proc Natl Acad Sci USA, 2014. 111(1): p. 125-30.
68. Bundy, B. C., M. J. Franciszkowicz, and J. R. Swartz, *Escherichia coli*-based cell-free synthesis of virus-like particles. Biotechnol Bioeng, 2008. 100(1): p. 28-37.
69. Caschera, F. and V. Noireaux, Synthesis of 2.3 mg/ml of protein with an all *Escherichia coli* cell-free transcription-translation system. Biochimie, 2014. 99: p. 162-8.
70. Calhoun, K. A. and J. R. Swartz, An economical method for cell-free protein synthesis using glucose and nucleoside monophosphates. Biotechnol Prog, 2005. 21(4): p. 1146-53.
71. Calhoun, K. A. and J. R. Swartz, Energizing cell-free protein synthesis with glucose metabolism. Biotechnol Bioeng, 2005. 90(5): p. 606-13.
72. Lian, Q., H. Cao, and F. Wang, The cost-efficiency realization in the *Escherichia coli*-based cell-free protein synthesis systems. Appl Biochem Biotechnol, 2014. 174 (7): p. 2351-67.
73. Zawada, J. F., et al., Microscale to manufacturing scale-up of cell-free cytokine production—a new approach for shortening protein production development timelines. Biotechnol Bioeng, 2011. 108(7): p. 1570-8.
74. Stech, M., et al., Cell-free systems: functional modules for synthetic and chemical biology. Adv Biochem Eng Biotechnol, 2013. 137: p. 67-102.
75. Brodel, A. K., D. A. Wustenhagen, and S. Kubick, Cell-free protein synthesis systems derived from cultured Mammalian cells. Methods Mol Biol, 2015. 1261: p. 129-40.
76. Stech, M., et al., A continuous-exchange cell-free protein synthesis system based on extracts from cultured insect cells. PLoS One, 2014. 9(5): p. e96635.
77. Kubick, S., et al., In vitro synthesis of posttranslationally modified membrane proteins. Current Topics in Membranes, 2009. 63(2): p. 25-49.
78. Guarino, C. and M. P. DeLisa, A prokaryote-based cell-free translation system that efficiently synthesizes glycoproteins. Glycobiology, 2012. 22(5): p. 596-601.
79. Ollis, A. A., et al., Substitute sweeteners: diverse bacterial oligosaccharyltransferases with unique N-glycosylation site preferences. Sci Rep, 2015. 5: p. 15237.
80. Ollis, A. A., et al., Engineered oligosaccharyltransferases with greatly relaxed acceptor-site specificity. Nat Chem Biol, 2014. 10(10): p. 816-22.
81. Dennis, D. T., et al., Tularemia as a biological weapon: medical and public health management. Jama, 2001. 285(21): p. 2763-73.
82. Prior, J. L., et al., Characterization of the O antigen gene cluster and structural analysis of the O antigen of *Francisella tularensis* subsp. *tularensis*. J Med Microbiol, 2003. 52(Pt 10): p. 845-51.
83. Ma, Z., et al., Glycoconjugate vaccine containing *Escherichia coli* O157:H7 O-antigen linked with maltose-binding protein elicits humoral and cellular responses. PLoS One, 2014. 9(8): p. e105215.
84. Jansson, P. E., et al., Structural studies of the *Escherichia coli* O78 O-antigen polysaccharide. Carbohydr Res, 1987. 165(1): p. 87-92.
85. Nothaft, H., et al., Study of free oligosaccharides derived from the bacterial N-glycosylation pathway. Proc Natl Acad Sci USA, 2009. 106(35): p. 15019-24.
86. Young, N. M., et al., Structure of the N-linked glycan present on multiple glycoproteins in the Gram-negative bacterium, *Campylobacter jejuni*. Journal of Biological Chemistry, 2002. 277(45): p. 42530-9.
87. Fisher, A. C., et al., Production of secretory and extracellular N-linked glycoproteins in *Escherichia coli*. Appl Environ Microbiol, 2011. 77(3): p. 871-81.
88. Oyston, P. C., A. Sjostedt, and R. W. Titball, Tularaemia: bioterrorism defence renews interest in *Francisella tularensis*. Nat Rev Microbiol, 2004. 2(12): p. 967-78.
89. Chen, L., et al., Outer membrane vesicles displaying engineered glycotopes elicit protective antibodies. Proc Natl Acad Sci USA, 2016. 113(26): p. E3609-18.
90. Kumru, O. S., et al., Vaccine instability in the cold chain: mechanisms, analysis and formulation strategies. Biologicals, 2014. 42(5): p. 237-59.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for synthesizing an N-glycosylated carrier protein for a polysaccharide via coordinated transcription, translation, and N-glycosylation in vitro, the method comprising:
   A) providing, in a single reaction vessel, a cell-free transcription, translation, and glycosylation reaction mixture, the cell-free reaction mixture comprising:
   (i) a transcription template encoding the carrier protein, the carrier protein comprising an inserted consensus sequence, N-X-S/T, wherein X may be any natural or unnatural amino acid except proline;
   (ii) an exogenous lipid-linked oligosaccharide (LLO) comprising a bacterial O-antigen;
   (iii) an exogenous oligosaccharide transferase (OST) that facilitates transfer of the O-antigen to the consensus sequence on the carrier protein;
   (iv) lysate enriched in the LLO of (ii) and the OST of (iii), and comprising endogenous transcription and translation components, wherein the lysate is derived from one or more engineered *Escherichia coli* (*E. coli*) strains, wherein at least one engineered *E. coli* strain produces the exogenous OST of (iii), and at least one engineered *E. coli* strain produces the exogenous LLO of (ii);

B) transcribing and translating the carrier protein in the cell-free reaction mixture;

C) glycosylating the carrier protein in the cell-free reaction mixture with the bacterial O-antigen.

2. The method of claim 1, wherein the bacterial O-antigen is from *Escherichia coli* (*E. coli*).

3. The method of claim 1, wherein the bacterial O-antigen is from Franciscella *tularensis*.

4. The method of claim 1, further comprising formulating the N-glycosylated carrier protein as an antigenic composition comprising the N-glycosylated carrier protein.

5. The method of claim 1, further comprising formulating the N-glycosylated carrier protein a vaccine composition comprising the N-glycosylated carrier protein.

6. The method of claim 1, wherein the carrier protein is an engineered variant of *E. coli* maltose binding protein (MBP), wherein the engineered variant comprises the inserted consensus sequence.

7. The method of claim 1, wherein the carrier protein is selected from a detoxified variant of the toxin from *Clostridium tetani*, a detoxified variant of the toxin from *Corynebacterium diptheriae, Haemophilus influenzae* protein D (PD), and a variant of *Neisseria meningitidis* porin protein (PorA), wherein the variants comprise the inserted consensus sequence.

8. The method of claim 1, wherein the glycosylating step utilizes an oligosaccharyltransferase (OST) which is a naturally occurring bacterial homolog of *Campylobacter jejuni* (*C. jejuni*) PglB.

9. The method of claim 1, wherein the glycosylating step utilizes an OST that is an engineered variant of *C. jejuni* PglB.

10. The method of claim 1, wherein the glycosylating step utilizes an OST that is a naturally occurring archaeal OST.

11. The method of claim 1, wherein the glycosylating step utilizes an OST which is a naturally occurring single-subunit eukaryotic OST.

12. The method of claim 1, wherein the one or more engineered *E. coli* strains comprises an inactivating modification or deletion in an endogenous waal gene.

13. The method of claim 1, wherein the cell lysate has an endotoxin unit (EU) concentration of less than about 180,000 EU/ml.

14. A kit for synthesizing a N-glycosylated carrier protein in vitro, the kit comprising as components:

(i) one or more cell lysates, wherein the one or more cell lysates are enriched in an orthogonal oligosaccharyltransferase (OST) and an O-antigen;

(ii) a transcription template encoding a carrier protein, the carrier protein comprising an inserted consensus sequence, N-X-S/T, wherein X may be any natural or unnatural amino acid except proline.

15. The kit of claim 14 comprising one cell lysate prepared from a single source strain, wherein the orthogonal OST and the O-antigen are present in the one cell lysate.

16. The kit of claim 14 comprising two cell lysates prepared from two source strains, wherein the orthogonal OST is present in one cell lysate of the two cell lysates and the O-antigen is present in the other cell lysate of the two cell lysates.

17. The kit of claim 14, wherein OST is produced from a source strain that overexpresses a gene encoding the orthogonal OST.

18. The kit of claim 14, wherein the O-antigen is produced from a source strain that overexpresses a synthetic glycosyltransferase pathway for producing the O-antigen.

19. A cell-free reaction mixture comprising an N-glycosylated carrier protein, wherein the N-glycosylated carrier protein is synthesized via a method comprising coordinated transcription, translation, and N-glycosylation in vitro, the method comprising:

A) providing, in a single reaction vessel, a cell-free transcription, translation, and glycosylation reaction mixture, the cell-free reaction mixture comprising:

(i) a transcription template encoding the carrier protein, the carrier protein comprising an inserted consensus sequence, N-X-S/T, wherein X may be any natural or unnatural amino acid except proline;

(ii) an exogenous lipid-linked oligosaccharide (LLO) comprising a bacterial O-antigen;

(iii) an exogenous oligosaccharide transferase (OST) that facilitates transfer of the O-antigen to the consensus sequence on the carrier protein;

(iv) lysate enriched in the LLO of (ii) and the OST of (iii), and comprising endogenous transcription and translation components, wherein the lysate is derived from one or more engineered *Escherichia coli* (*E. coli*) strains, wherein at least one engineered *E. coli* strain produces the exogenous LLO of (ii), and at least one engineered *E. coli* strain produces the exogenous OST of (iii), wherein the one or more engineered *E. coli* strains comprise an inactivating modification or deletion in an endogenous waaL gene;

B) transcribing and translating the carrier protein in the cell-free reaction mixture;

C) glycosylating the carrier protein in the cell-free reaction mixture the bacterial O-antigen.

20. A method of vaccinating a subject in need thereof against a bacterial O-antigen, the method comprising administering to the subject the cell-free reaction mixture of claim 19 and/or a purified N-glycosylated carrier protein therefrom.

21. The method of claim 5, wherein the vaccine composition further comprises an adjuvant.

* * * * *